US012736476B2

(12) United States Patent
Vasefi et al.

(10) Patent No.: US 12,736,476 B2
(45) Date of Patent: Sep. 15, 2026

(54) SYSTEM AND METHOD FOR ASSESSING PRODUCT

(71) Applicant: SafetySpect Inc., Grand Forks, ND (US)

(72) Inventors: Fartash Vasefi, Sherman Oaks, CA (US); Kenneth Edward Barton, Palm City, FL (US); Gregory Bearman, Pasadena, CA (US); Hossein Kashani Zadeh, Grand Forks, ND (US); Alireza Akhbardeh, Daily City, CA (US)

(73) Assignee: SafetySpect Inc., Sherman Oaks, CA (US)

( * ) Notice: Subject to any disclaimer, the term of this patent is extended or adjusted under 35 U.S.C. 154(b) by 482 days.

(21) Appl. No.: 17/980,996

(22) Filed: Nov. 4, 2022

(65) Prior Publication Data

US 2023/0142722 A1 May 11, 2023

Related U.S. Application Data

(60) Provisional application No. 63/397,761, filed on Aug. 12, 2022, provisional application No. 63/394,180, filed on Aug. 1, 2022, provisional application No. 63/276,046, filed on Nov. 5, 2021.

(51) Int. Cl.

| | |
|---|---|
| ***G01N 21/64*** | (2006.01) |
| ***G01N 21/55*** | (2014.01) |
| ***G01N 33/12*** | (2006.01) |
| *G01N 21/31* | (2006.01) |
| *G01N 33/02* | (2006.01) |

(52) U.S. Cl.

CPC ......... *G01N 21/6486* (2013.01); *G01N 21/55* (2013.01); *G01N 21/6456* (2013.01); *G01N 33/12* (2013.01); *G01N 21/31* (2013.01); *G01N 33/02* (2013.01)

(58) Field of Classification Search

USPC ........................................................... 702/81

See application file for complete search history.

(56) References Cited

U.S. PATENT DOCUMENTS

| | | | | |
|---|---|---|---|---|
| 11,454,496 | B2 * | 9/2022 | Lee | G01J 3/4406 |
| 2004/0245350 | A1 * | 12/2004 | Zeng | A61B 1/042 236/77 |
| 2005/0195389 | A1 * | 9/2005 | Noy | G01N 21/956 356/237.2 |

(Continued)

*Primary Examiner* — Paul D Lee

(74) *Attorney, Agent, or Firm* — Jason T. Daniel, Esq.; Daniel Law Offices, P.A.

(57) ABSTRACT

A system for assessing biological tissue is disclosed. The system contains an illumination hardware arrangement comprising transmission and sensing hardware, the illumination hardware arrangement configured to inspect a product using three modes from a group containing: a first fluorescence imaging mode; a second fluorescence imaging mode; and a reflectance imaging mode; and processing hardware configured to operate the illumination hardware arrangement according to a protocol containing inspection settings of the three modes, wherein the processing hardware receives scan results for the three modes from the illumination hardware arrangement and identifies attributes of the product by constructing a dataset from the scan results for three two modes and analyzing the dataset.

15 Claims, 24 Drawing Sheets

(56) References Cited

U.S. PATENT DOCUMENTS

| | | | | |
|---|---|---|---|---|
| 2008/0177140 | A1* | 7/2008 | Cline | A61B 1/0646<br>600/112 |
| 2008/0225272 | A1* | 9/2008 | Nishimura | G01N 21/6458<br>356/73 |
| 2015/0377787 | A1* | 12/2015 | Zeng | A61B 5/0071<br>356/301 |
| 2018/0264347 | A1 | 9/2018 | Tran et al. | |
| 2019/0293620 | A1* | 9/2019 | Farkas | G01N 21/3563 |
| 2022/0187847 | A1 | 6/2022 | Cella et al. | |
| 2024/0153289 | A1* | 5/2024 | Masaeli | G06V 20/695 |

* cited by examiner

SYSTEM AND METHOD FOR ASSESSING PRODUCT

CROSS REFERENCE TO RELATED APPLICATIONS

This application claims the benefit of U.S. Provisional Application No. 63/276,046, filed on Nov. 5, 2021, which is incorporated herein by reference in its entirety. This application claims the benefit of U.S. Provisional Application No. 63/394,180, filed on Aug. 1, 2022, which is incorporated herein by reference in its entirety. This application claims the benefit of U.S. Provisional Application No. 63/397,761, filed on Aug. 12, 2022, which is incorporated herein by reference in its entirety.

FIELD

The present invention relates to a system and method for assessing product. More particularly, the present invention relates to a non-invasive imaging system and method for assessing a product.

BACKGROUND

With increased product imports and limited monitoring, fraud is a growing concern for consumers. This is of special concern when imported product is food related. Fraud in food industry raises concern for food safety and food quality.

For example, seafood is highly vulnerable to fraud due to factors such as the similar appearance of many species, variation in prices, complex supply chains, and challenges with supply and demand. Although instances of seafood fraud are sometimes reported, many incidents go undetected and the full extent of seafood fraud is difficult to determine.

The flesh of many fish species is similar in taste and texture and, therefore, it is difficult to identify species in fillet form, especially after preparation for consumption. It can be relatively easy to substitute an inexpensive species for one of higher value. One survey by the National Marine Fisheries Service's National Seafood Inspection Laboratory (NSIL) found that 37% of fish and 13% of other seafood (e.g., shellfish, edible seaweed) from randomly selected vendors were mislabeled.

Current techniques for detection of species substitution and mislabeling of fish are laboratory-based methods that typically require hours and/or days for species detection. For example, the Food and Drug Administration (FDA) utilizes a DNA sequencing method called DNA barcoding, which has been found to be highly accurate at differentiating most species of fish. This method is advantageous in that it can target a wide range of species simultaneously. However, this method typically requires hours and/or days to achieve results and involves many laboratory steps for its completion. Furthermore, this method is not ideal for onsite testing, for example at fish processing facilities, because it involves expensive equipment and technical expertise. Instead, samples must be shipped to a commercial laboratory that perform the technique.

Due to the globalized nature and complexity of supply chains, the detection of product mislabeling, and quality requires innovative approaches that can measure compositional and chemical characteristics of products. Inspection tools are needed to assess product fraud more comprehensively and mitigate its potential impacts.

SUMMARY

Generally speaking, pursuant to the various embodiments, according to one aspect, a system for assessing product is presently disclosed. The system comprises an illumination hardware arrangement comprising transmission and sensing hardware, the illumination hardware arrangement configured to inspect a product using three modes from a group comprising: a first fluorescence imaging mode; a second fluorescence imaging mode; and a reflectance imaging mode. The system further comprises processing hardware configured to operate the illumination hardware arrangement according to a protocol comprising inspection settings of the three modes, wherein the processing hardware receives scan results for the three modes from the illumination hardware arrangement and identifies attributes of the product by constructing a dataset from the scan results for three two modes and analyzing the dataset. According to another aspect, the product being assessed is a pharmaceutical product, a drug product, biological product, meat, seafood, a construction product, a natural product, or a synthetic product. According to another aspect, the processing hardware comprises a processor, at least one trained artificial intelligence module, and at least one classifier. According to another aspect, the protocol is determined in part based on an identification of particular attributes expected to be associated with the product when examined using the three modes. According to another aspect, the three modes are three spectroscopy modes.

According to another aspect, a product inspection apparatus is disclosed. The apparatus comprises an illumination hardware arrangement comprising transmission and sensing hardware, the illumination hardware arrangement configured to inspect a product using three modes from a group comprising: a first fluorescence imaging mode; a second fluorescence imaging mode; and a reflectance imaging mode. The apparatus further comprises processing hardware configured to operate the illumination hardware arrangement according to a protocol comprising inspection settings of the three modes, wherein the processing hardware receives scan results for the three modes from the illumination hardware arrangement and identifies attributes of the product by constructing a dataset from the scan results for three two modes and analyzing the dataset. According to another aspect, the product comprises a pharmaceutical product, a drug product, biological product, meat, seafood, a construction product, a natural product, or a synthetic product. According to another aspect, the processing hardware of the apparatus comprises a processor, at least one trained artificial intelligence module, and at least one classifier. According to another aspect, the protocol is determined in part based on an identification of particular attributes expected to be associated with the product when examined using the three modes. According to another aspect, the three modes are three spectroscopy modes. According to another aspect, the transmission hardware of the apparatus comprises one or more light sources. According to another aspect, the one or more light sources of the apparatus are light emitting diodes used in the first fluorescence imaging mode. According to another aspect, the one or more light sources of the apparatus are light emitting diodes used in the second fluorescence imaging mode. According to another aspect, the one or more light sources of the apparatus are bulbs used in the reflectance imaging mode. According to another aspect, the sensing hardware of the apparatus comprises at least two spectrometers. According to another aspect, the two spectrometers are used in the reflectance imaging mode. According to another aspect, one of two spectrometers is used in the first fluorescence imaging mode and the second fluorescence imaging mode.

These and other advantages of the present invention will become apparent to this skilled in the art from the following detailed description of the invention and the accompanying drawings.

Figure 1A:
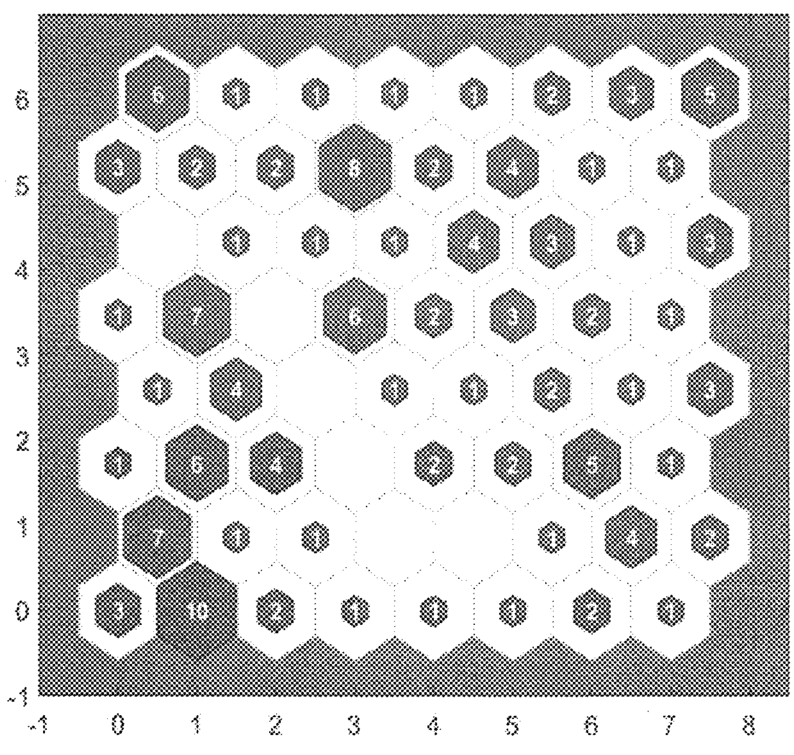
FIG. 1*a* depicts a plot of the number of input vectors mapped to each neuron according to some embodiments presently disclosed.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

As described herein, the term "pivotally connected" shall be used to describe a situation wherein two or more identified objects are joined together in a manner that allows one or both of the objects to pivot, and/or rotate about or in relation to the other object in either a horizontal or vertical manner.

As described herein, the term "removably coupled" and derivatives thereof shall be used to describe a situation wherein two or more objects are joined together in a non-permanent manner so as to allow the same objects to be repeatedly joined and separated.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software-based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Although some of the presently disclosed embodiments pertains to testing seafood related products, it is to be understood that presently disclosed embodiments may be applied to other products such as, for example, food related products, pharmaceutical related products, drug related products, meat (i.e. beef, lamb, pork, poultry), seafood (i.e. fish, shellfish, seaweed), construction related products, natural products, biological products, synthetic products, pharmaceutical related products, drug related products, and/or other consumer related products.

According to some embodiments, presently disclosed system and method use Quality, Adulteration and Traceability (QAT) system for management of products supply chains. For food related products, QAT provides species identification, ability to incorporate many species (unlike rapid DNA analysis), bypasses sample preparation, and reduces the time and cost of species identification. According to some embodiments, QAT uses multimode spectroscopy, combining reflectance and fluorescence-based spectral analysis and a fusion AI classification algorithm.

According to some embodiments, presently disclosed system and method can be used to track products such as food related products from harvest to market, add quality and freshness assessment with the same hardware platform.

By providing product data about product(s) and quality, presently disclosed system and method may be used to identify mislabelled product, and may be used to dynamically price perishable food related products at multiple purchase decision points—beyond traditional final-discounting by retailers.

According to some embodiments, presently disclosed system and method may be used, for example, 1) to provide rapid species identification; 2) to provide scalability to incorporate many species (unlike rapid DNA analysis which is limited to testing a single target species); 3) to bypass the need for sample preparation, and reducing the time and cost of species identification; 4) to work with cloud-based and/or blockchain food supply chain management; and/or 5) to asses quality in real time to enable dynamic pricing at multiple points along the seafood supply chain.

According to some embodiments, presently disclosed system and method may be used to optically detect established chemical signatures of products (such as, for example, seafood species) and quality by integrating several types of spectroscopic data through fusion-artificial intelligence (AI) algorithm into one or more reports. According to some embodiments, presently disclosed system and method may utilize a handheld device for onsite spot-checks of species-ID and quality across, for example, the seafood supply chain.

According to some embodiments, presently disclosed system and method generates a spectral database for one or more products. The one or more products are imaged using reference spectroscopic systems including visible and near infrared (VIS-NIR), Fluorescence, and short-wave infrared (SWIR) to determine spectral characteristics of the one or more products. The spectral characteristics may indicate species of the one or more products, quality and/or nutrient content of the one or more products. According to some embodiments, after one or more products are imaged, data (i.e. results) that are generated may be corrected for instrument response and/or ambient light. The data may also be normalized using, for example, a reference white target.

According to some embodiments, presently disclosed system and method may analyze data using for example, support vector machine (SVM) with a radial basis function, cubic support vector machine (SVM), weighted K-nearest neighbor (WKNN), linear discriminant (LD), and/or Gaussian Naïve Bayes (GNB).

The sensitivity (min, max)/specificity (min, max) ranges may be from VIS-NIR (7%, 100%)/(97%, 100%), Fluorescence (7%, 100%)/(97%, 100%), SWIR (0%, 97%)/(97%, 100%) to multimode data with (81%, 100%)/(99%, 100%).

According to some embodiments, presently disclosed system and method may utilize Deep Learning methods (e.g. Long Short-Term Memory neural network and Reinforcement learning) combined with a weighting score optimization in the fusion classifier. Long short-term memory (LSTM) is an artificial recurrent neural network (RNN) architecture used in the field of deep learning.

According to some embodiments, presently disclosed system and method may use VIS-NIR and SWIR spectroscopic system with integrated light source, Raspberry Pi computer, and fiber sampling head with reflective optics. The entire spectral range may be simultaneously measured by two spectrometers (UVVIS with a spectral range from 250 nm to 1050 nm with spectral resolution <8 nm FWHM and NIR from 900 nm to 1700 nm with spectral resolution <16 nm FWHM).

According to some embodiments, presently disclosed system and method may use a fluorescence spectroscopy system with excitation filter wavelength at 380 nm, variable excitation power up to 2 W, integrated QR Code reader, rechargeable Li-Ion battery, and/or Capacitive Touch Display.

Hyperspectral band selection is the process of selecting an optimal set of narrow wavelength bands from a large number over a broad range, typically for one of two purposes: hyperspectral reconstruction or classification. The former seeks to condense the information content of the full resolution spectrum so that the spectrum may be reconstructed from a relatively small subset of wavelength bands. The latter seeks to enable classification based on features contained within this small subset.

According to some embodiments, presently disclosed system and method provides self-organizing map weight plane distance (SOM WPD) method for automated band selection based on analysis of the weight planes from a trained self-organizing map.

According to some embodiments, presently disclosed system and method may generate a detailed spectrum at each pixel in the image, thus achieving high resolution in both the spatial and spectral dimensions. By exploiting the unique spectral characteristics of different materials, presently disclosed system provides the capability to identify and distinguish materials spatially in imagery.

Self-organizing maps (SOMs) identify a nonlinear transformation from high to low dimensional space such that the separation between points in the lower dimension is representative of the relative dissimilarity between their higher dimensional counterparts. The Feature Competitive Algorithm (FCA) is a general feature selection method that works by identifying those features in the original high dimensional space that align best with the trained "reference vectors" of the SOM. The Subspace Clustering Based on SOM (SCBSOM) method applies a one-dimensional clustering in each dimension based on the weight connections in the learned SOM followed by a merging process. Heuristic Input for SOM (HI-SOM) similarly applies clustering in the trained SOM for feature selection.

According to some embodiments, presently disclosed system and method uses hyperspectral band selection method based on the exploitation of the relationships between weights in the trained SOM's reference vectors. The mean distance between pairs of "weight planes" (i.e., a high dimensional plane formed by the weights from all trained reference vectors corresponding to the same input band) is used as a measure of the nonlinear correlation between the bands. This measure as the Weight Plan Distance (WPD). This method may be applied to a food fraud application where hyperspectral imaging is used to determine the correct species of, for example, fish fillets.

Developed by Teuvo Kohonen in 1982, the SOM is a type of two-layer artificial neural network that produces a low-dimensional (typically 2D) representation of vectors in a high-dimensional input feature space. It does this by applying unsupervised competitive learning to move the network's weights closer to the input vector. For each input vector, the Euclidian distance between this vector and the weight vectors (called "reference vectors") for all output neurons is calculated. The neuron with the smallest distance is declared the "best matching unit" (BMU), and the reference vectors for all neurons within a neighborhood of the BMU are updated. This "neighborhood" is defined with a neighborhood function, $h_{ci}(t)$, where the c subscript refers to the index of the BMU and the i subscript refers to the $i^{th}$ neuron[24]. The updated weight for the $i^{th}$ reference vector is then given by formula (1) below.

$$w_i(t+1)=w_i(t)+a\cdot h_{ci}(t)\cdot[x(t)-w_i(t)] \quad (1)$$

Figure 1B:
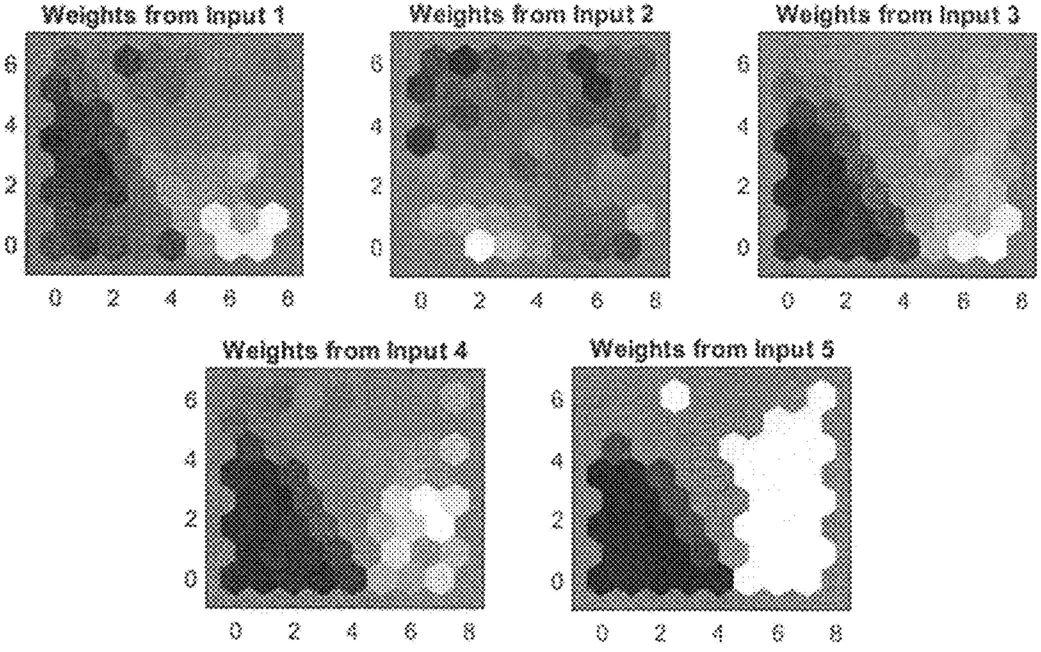
FIG. 1*b* depicts plots of weight values for each input weight plane according to some embodiments presently disclosed.

FIGS. 1*a-b* depict the results of training an 8×8 SOM on Fisher's iris dataset. The output layer neurons may be arranged in a hexagonal pattern. FIG. 1*a* shows a plot of the number of input vectors that are mapped to each output layer neuron. FIG. 1*b* shows plots of the reference vector weight values at each output neuron for each input weight, with darker colors representing larger values. The collection of weight values for each input may be referred to as a "component plane" or "weight plane".

The weight plane distances (WPD) may be computed by calculating the squared difference between the value of a node in one weight plane and the corresponding node in another weight plane. This calculation may be repeated for all nodes, and the squared differences are then averaged to yield the WPD between these two weight planes. The complete set of WPDs may be computed by calculating the WPD between each pair of weight planes. This WPD set would yield a symmetric N×N matrix, where N is the number of nodes in the SOM.

According to some embodiments, presently disclosed system and method provide a means of band selection based on minimization of redundancy, and it also provides a measure of importance for exact band selection. For example, a tall but broad peak in the WPD matrix suggests that selecting any pair of bands in the vicinity of the true local optimum and still achieve a near-maximum degree of non-redundancy. This could be particularly beneficial in designing a sparse hyperspectral imaging system where the collection of imagery at certain wavelengths may be easier to engineer than at others.

To select features using the WPD matrix, presently disclosed system and method may find local peaks along each row of the WPD matrix. The WPD values at these peak locations are saved in an intermediate matrix while the values at other locations are zeroed. Similar process may be applied along each column of this intermediate matrix to identify the final WPD peaks. A two-stage process may be applied to better eliminate the false peaks that can appear when using 2D peak finder algorithms.

The bands selected the SOM-based method may be used as features to train one or more machine learning classifiers—linear discriminant, quadratic support vector machine (SVM), weighted k-nearest neighbors (WKNN), and/or subspace discriminant (an ensemble method which applies linear discriminants to random subsets of features). One or more of these classifiers may be used to classify the correct species of food product such as, for example, fish fillet based on information from one pixel's visible/near-infrared (VNIR) reflectance or fluorescence spectrum. This classification may be repeated for numbers of selected wavelengths, k=3, 4, and 5, and a 5-fold cross-validation may be conducted as a robust estimation of classification accuracy.

Figure 2:
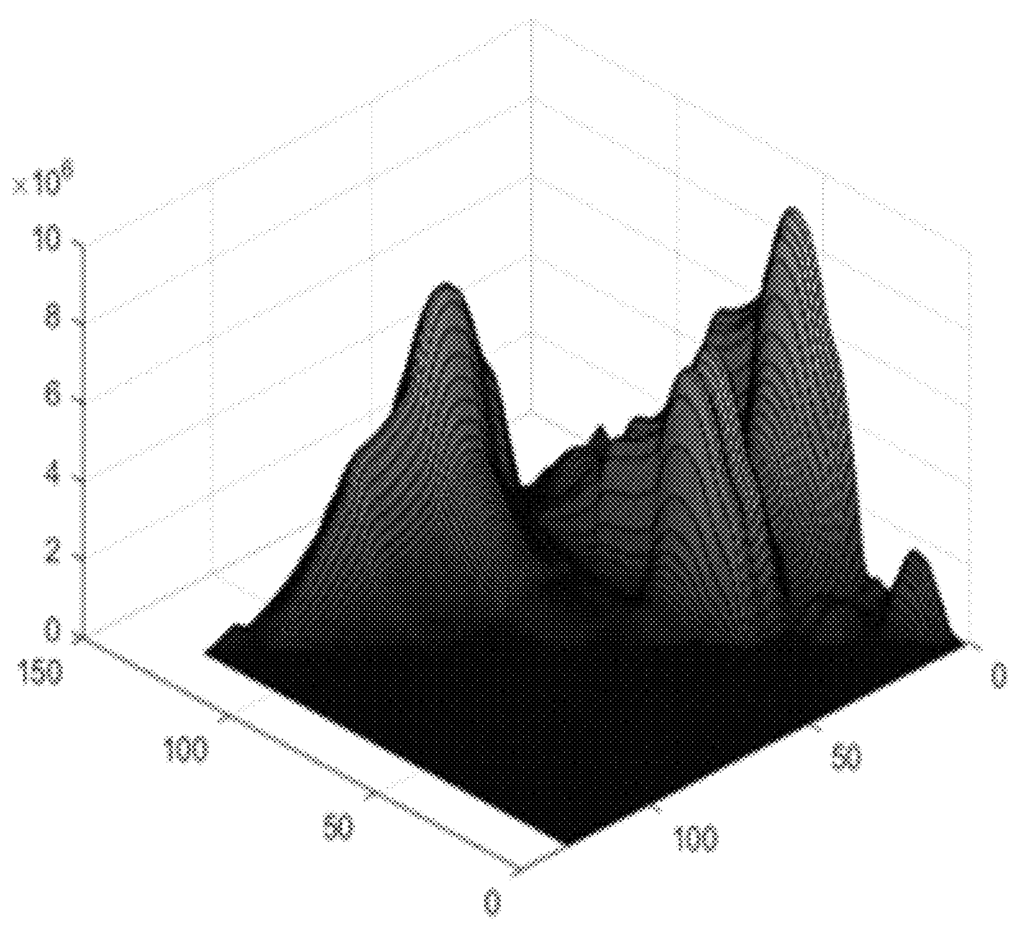
FIG. 2 depicts surface plot of weight plane distance (WPD) from visible and near-infrared (VNIR) data according to some embodiments presently disclosed.

Feature ranking may be conducted using the WPD values at the selected peaks. For example, the two features corresponding to the tallest peak in FIG. 2 (i.e., the two features with the largest WPD) may be assigned ranks one and two. The two features corresponding to the next tallest peaks may be assigned ranks three and four, and so on.

Figure 3:
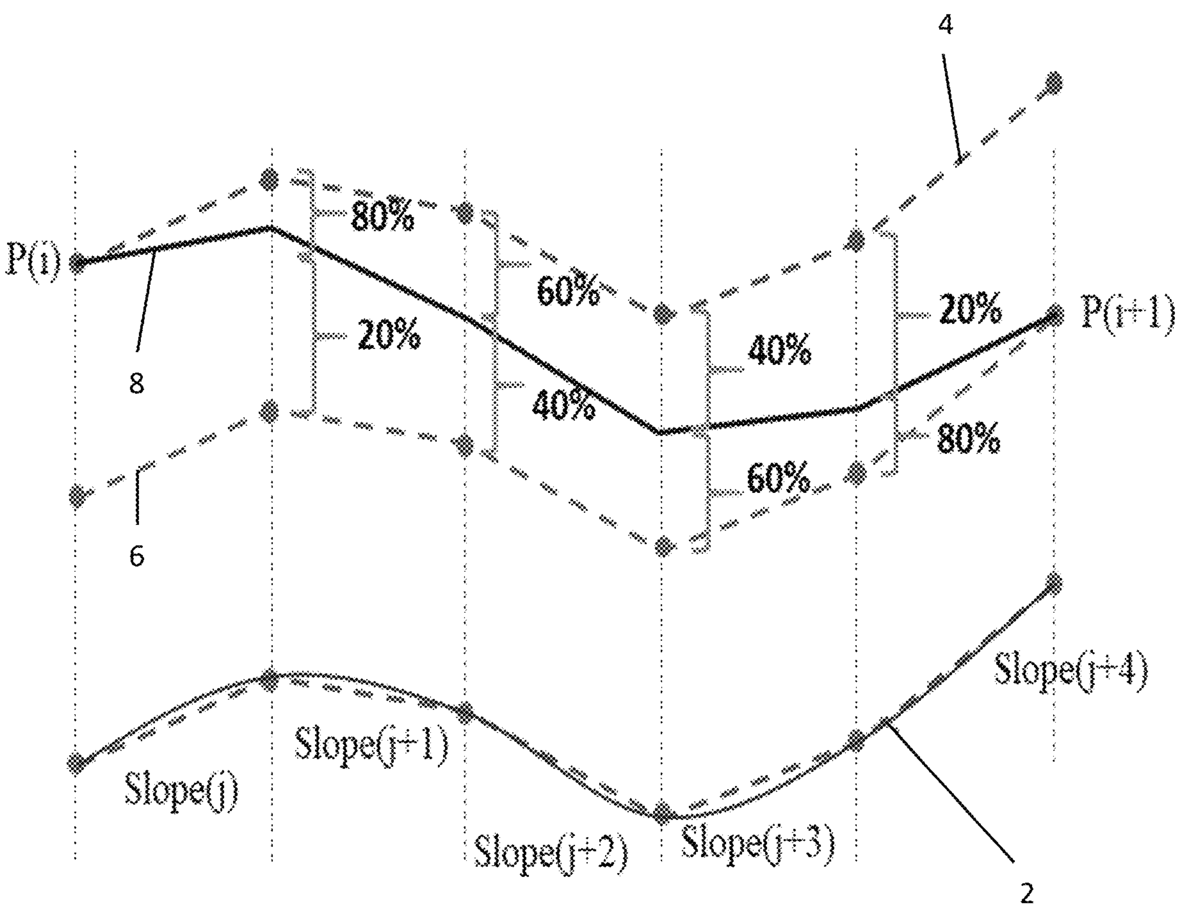
FIG. 3 depicts spectral reconstruction algorithm according to some embodiments presently disclosed.

According to some embodiments, presently disclosed system and method may use a spectral reconstruction algorithm based on samples taken at a small number of wavelength bands, k, within the relevant spectral range and a full-resolution spectral average taken over the entire scene. The scene is a homogenous region of the sample being analyzed (no background regions). This spectral average is referred to as the "reference spectrum" and may be used to estimate the reflectance/fluorescence values at the missing N-k wavelengths. This interpolation may be conducted in a piecewise linear manner by fixing the values at the sampled wavelength band centers and using the point-to-point slopes from the corresponding region of the reference spectrum to estimate values at wavelengths in between in both the forward (i.e., increasing wavelengths) and backward directions. A weighted average of the corresponding points from these spectrum estimates yields the resulting reconstruction. This process may be repeated for every pair of successive sampled bands until the entire spectral range has been covered. Values below the lowest selected wavelength band and above the highest are estimated using a single backward or forward projection, respectively. FIG. 3 depicts spectrum values sampled at bands indicated by points P(i) and P(i+1). Point-to-point slopes at full resolution may be calculated from the reference spectrum line 2 and used to calculate a forward estimation line 4 anchored at P(i) and a backward estimation line 6 anchored at P(i+1). The final full resolution estimate line 8 may be determined by taking weighted averages of the forward line 4 and backward line 6 estimates.

Formula (2) below may be used to solve optimization problem.

$$\text{Minimize } f(x_k)=\Sigma_{j}=1^N(S(j)-P_{interp}(f))^2:$$

$$\text{Subject to:}\|x_k\|_0=k$$

$$1\leq x_k(l)\leq N\forall l\in 1,2,\ldots,k \quad (2)$$

$$x_k(l)\in\mathbb{Z}$$

Thus, it may be possible to find the k wavelength bands that minimize the sum of squared errors from the spectral reconstruction over the full-resolution spectral range. The first constraint in Formula (2) restricts the number of wavelength samples to no more than k. The second constraint in Formula (2) restricts the indices of the sampled wavelengths (which form the vector x) to fall within the bounds of the indices of the full-resolution spectrum (i.e., 1 and N). The third constraint in Formula (2) ensures that this vector is integer valued.

To improve the genetic algorithm's probability of finding the global minimum, presently disclosed system and method may use chromosome resulting from the k=m−1 iteration to inform the starting point for the k=m iteration (with the mth wavelength selected at random) and followed the genetic algorithm with a Generalized Pattern Search (GPS). The GPS algorithm creates a mesh centered on the starting point, defined by a set of direction vectors and a scalar mesh size. At each iteration, the objective function may be evaluated at each of the new points until one is found that produces a value less than the current minimum value. This new point may be selected as the new starting point, and the search continues with the same (or larger) mesh size. If none of the points produces a lower objective function value, then the mesh size may be reduced, and the process continues until the mesh size reaches a minimum threshold. In this manner, the GPS algorithm can help push the genetic algorithm solution out of a local optimum and move it to the global optimum (assuming these points are in the same vicinity).

According to some embodiments, presently disclosed system and method were used to create a database consisting of VNIR reflectance and fluorescence spectra collected from 14 fish fillets of six different species (six red snappers, four Malabar snappers, one vermillion snapper, one summer flounder, one blue tilapia, and one white bass). Each fillet was placed in a 150×100×25 $mm^3$ sample holder created with, for example, a 3D printer using production-grade black thermoplastic. Image acquisition used the pushbroom method whereby a linear motorized translation stage was used to move the sample holder incrementally across the scanning line of the imaging spectrograph. The length of the instantaneous field of view (IFOV) was made slightly longer than the length of the sample holder (150 mm) by adjusting the lens-to-sample distance. The resulting spatial resolution along this dimension was determined as 0.4 mm/pixel. Each fillet was sampled along the width direction (100 mm) of the holder with a step size of 0.4 mm to match the spatial resolution of the length direction.

Flat-field corrections may be applied to the VNIR reflectance images and the fluorescence images to convert original absolute intensities in CCD counts to relative reflectance and fluorescence intensities. An initial spatial mask may be created for each imaging mode to separate the fish fillets from the background. Outliers may be handled using data quality strategies such as, for example, by first calculating the mean (μ) and standard deviation (σ) of the fish pixel intensities over the entire fillet. According to some embodiments, presently disclosed system and method used 10×10-pixel region "blocks" to mimic independent fish fillet spectral point measurements using the field of view of a fiber optic spectrometer. According to some embodiments, presently disclosed system and method used, for example, an exclusion criterion where if ≥10% of the constituent pixels in a block exceeded μ±2 σ to eliminate outliers. This approach produced a final set of spatial masks, one each for the reflectance and fluorescence images, that determined the blocks for analysis. Table 1 lists the number of valid blocks for each fillet and each collection mode.

TABLE 1

| Fillet | Collection Mode | Number of Fillets | Number of Valid Blocks |
|---|---|---|---|
| Red Snapper | VNIR | 6 | 2,401 |
| Malabar Snapper | VNIR | 4 | 1,599 |
| Vermillion Snapper | VNIR | 1 | 283 |
| Summer Flounder | VNIR | 1 | 316 |
| Blue Tilapia | VNIR | 1 | 250 |
| White Bass | VNIR | 1 | 280 |
| Red Snapper | Fluorescence | 6 | 2,423 |
| Malabar Snapper | Fluorescence | 4 | 1,517 |
| Vermillion Snapper | Fluorescence | 1 | 504 |
| Summer Flounder | Fluorescence | 1 | 516 |
| Blue Tilapia | Fluorescence | 1 | 345 |
| White Bass | Fluorescence | 1 | 387 |

Figure 4A:
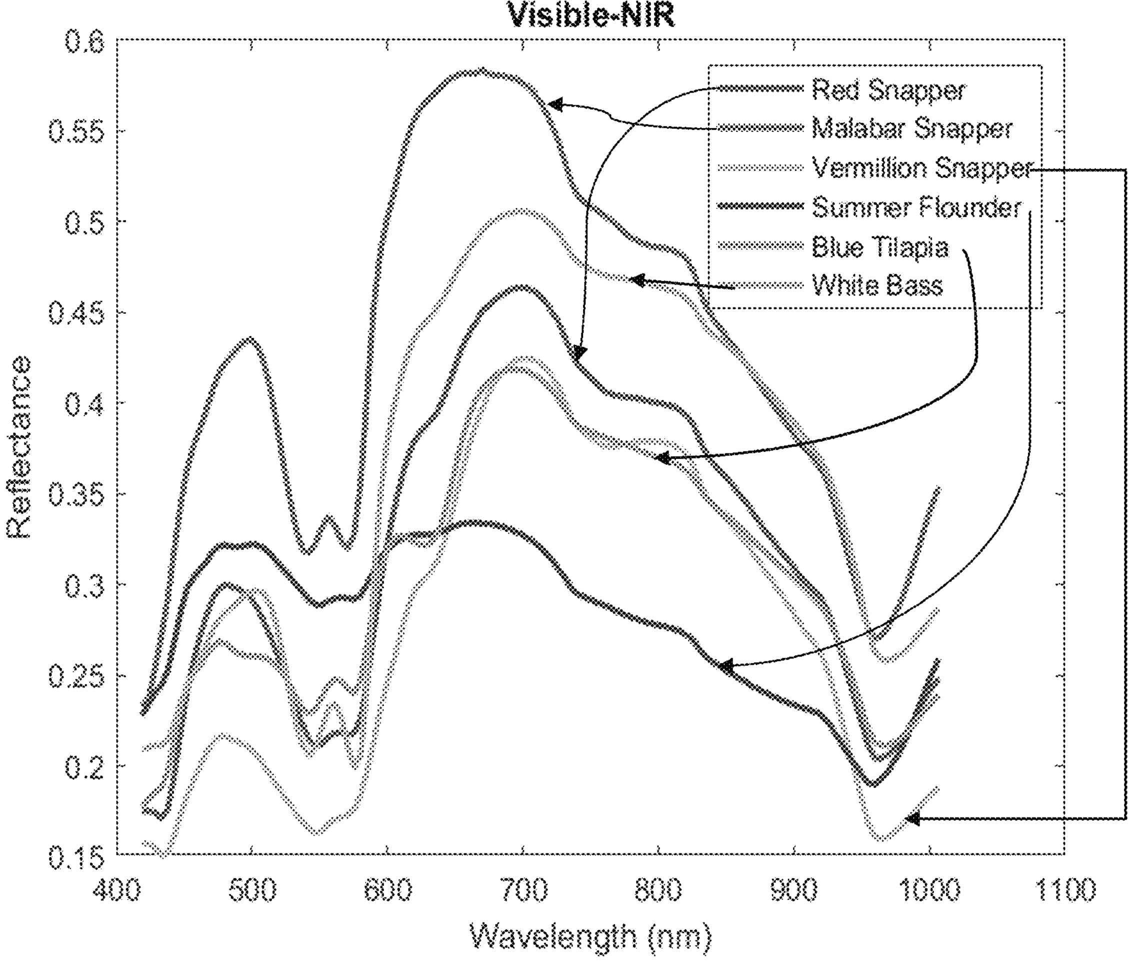
FIG. 4*a* depicts reflectance data for each of six fish according to some embodiments presently disclosed.
Figure 4B:
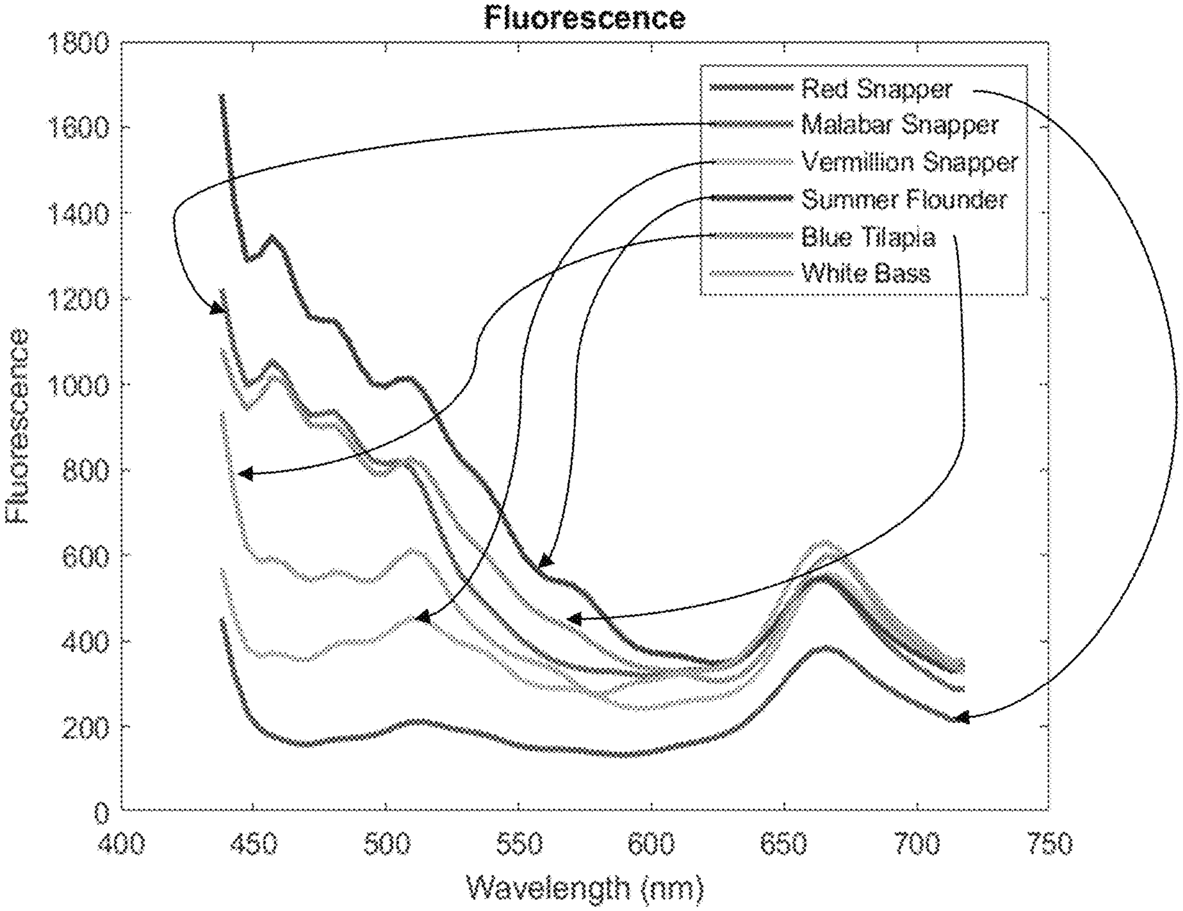
FIG. 4*b* depicts fluorescence spectra data for each of six fish according to some embodiments presently disclosed.
Figure 5A:
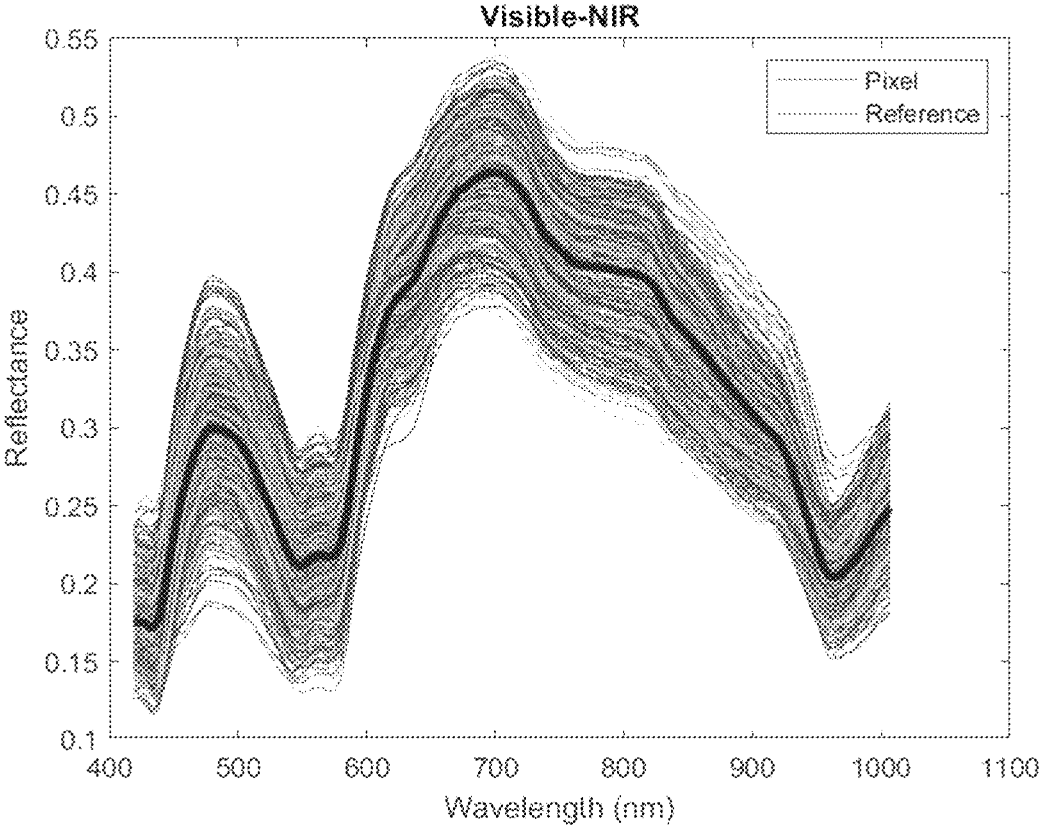
FIG. 5*a* depicts reflectance data for each pixel of one of the red snapper fillets according to some embodiments presently disclosed.
Figure 5B:
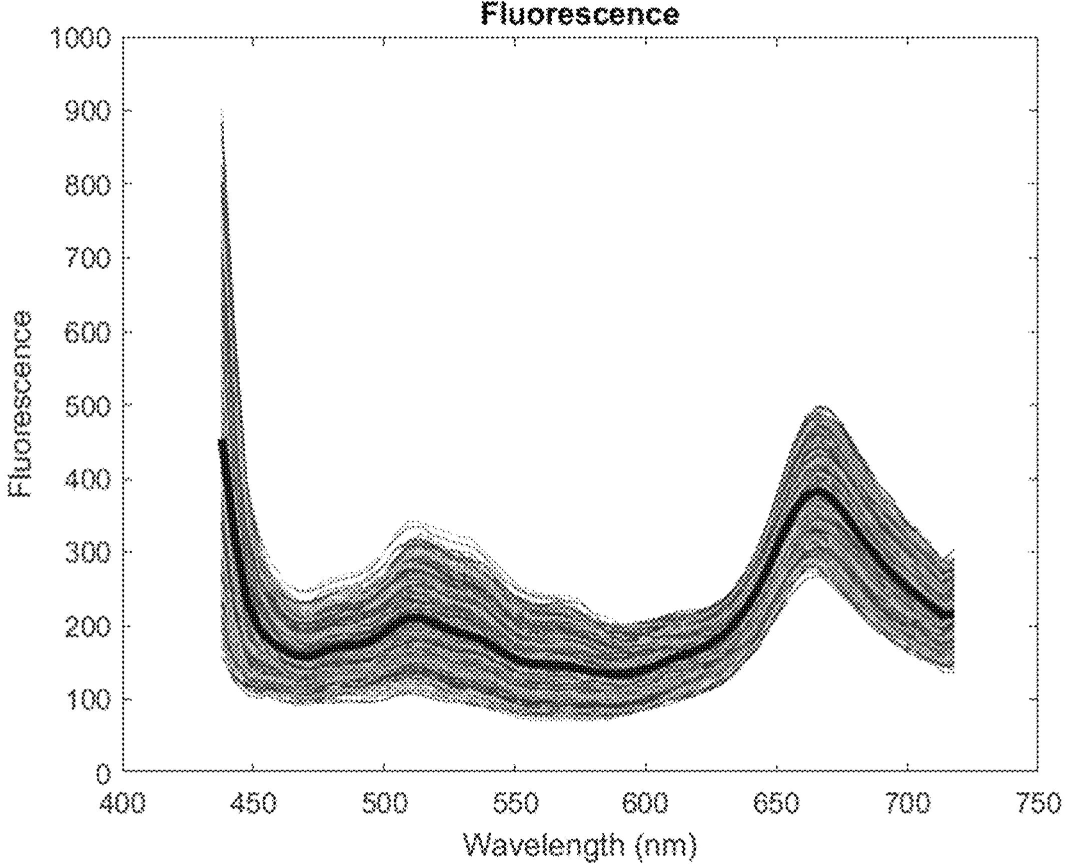
FIG. 5*b* depicts fluorescence spectra data for each pixel of one of the red snapper fillets according to some embodiments presently disclosed.

The average reflectance and fluorescence spectra for each of the six fish species are shown in FIGS. 4*a-b* respectively. The spectra for all six species (including the red snapper and the Malabar snapper) were calculated from the pixels of a single fillet. VNIR reflectance and fluorescence spectra for individual blocks from one red snapper image are shown in FIGS. 5*a-b*, along with the average spectrum. The significant differences in the shapes and positions of the spectral averages for the various species and homogeneous nature of the spectra for pixels of a single fillet suggest that high classification accuracies can be achieved with this spectral information.

Figure 6A:
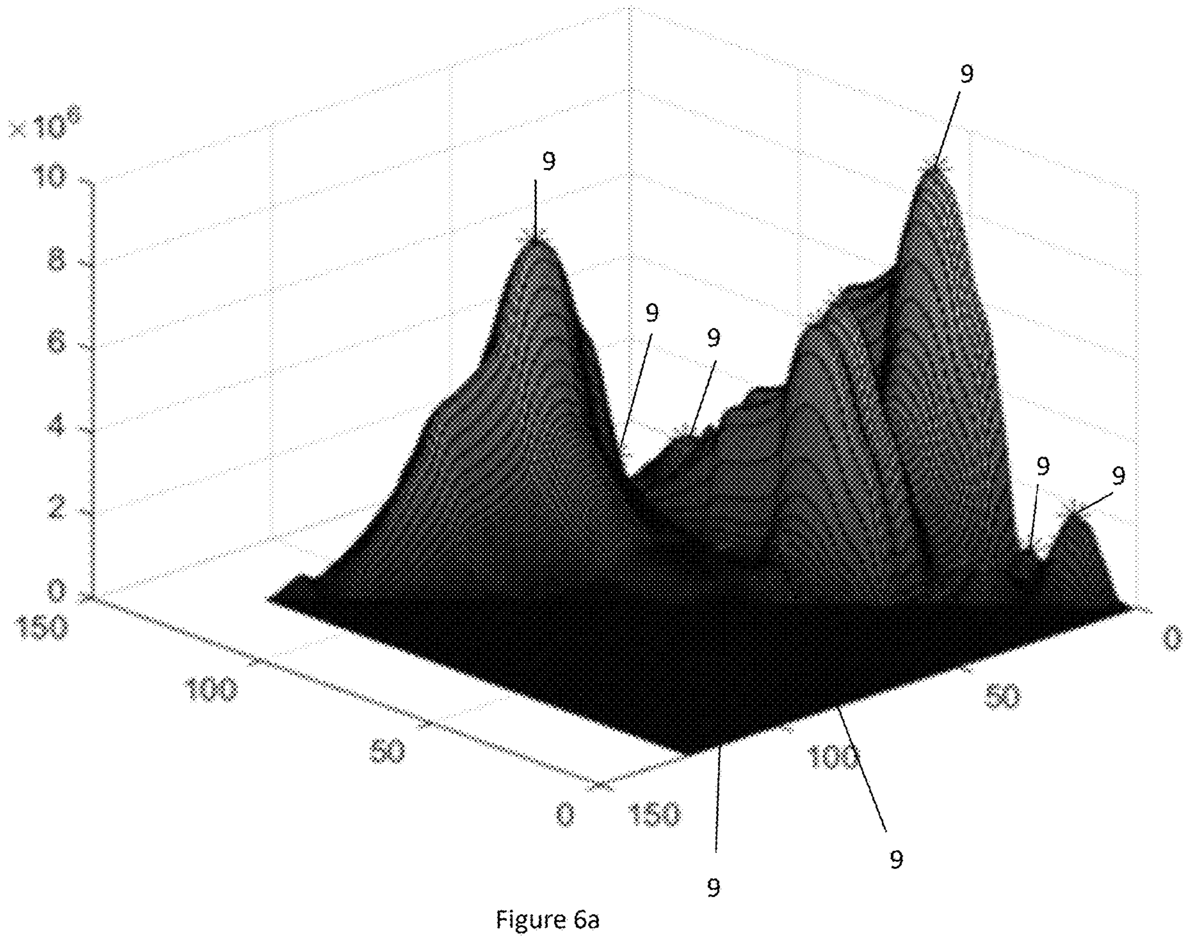
FIGS. 6*a-c* depict results of the peak finding algorithm for the VNIR data displayed from three different angles according to some embodiments presently disclosed.
Figure 6B:
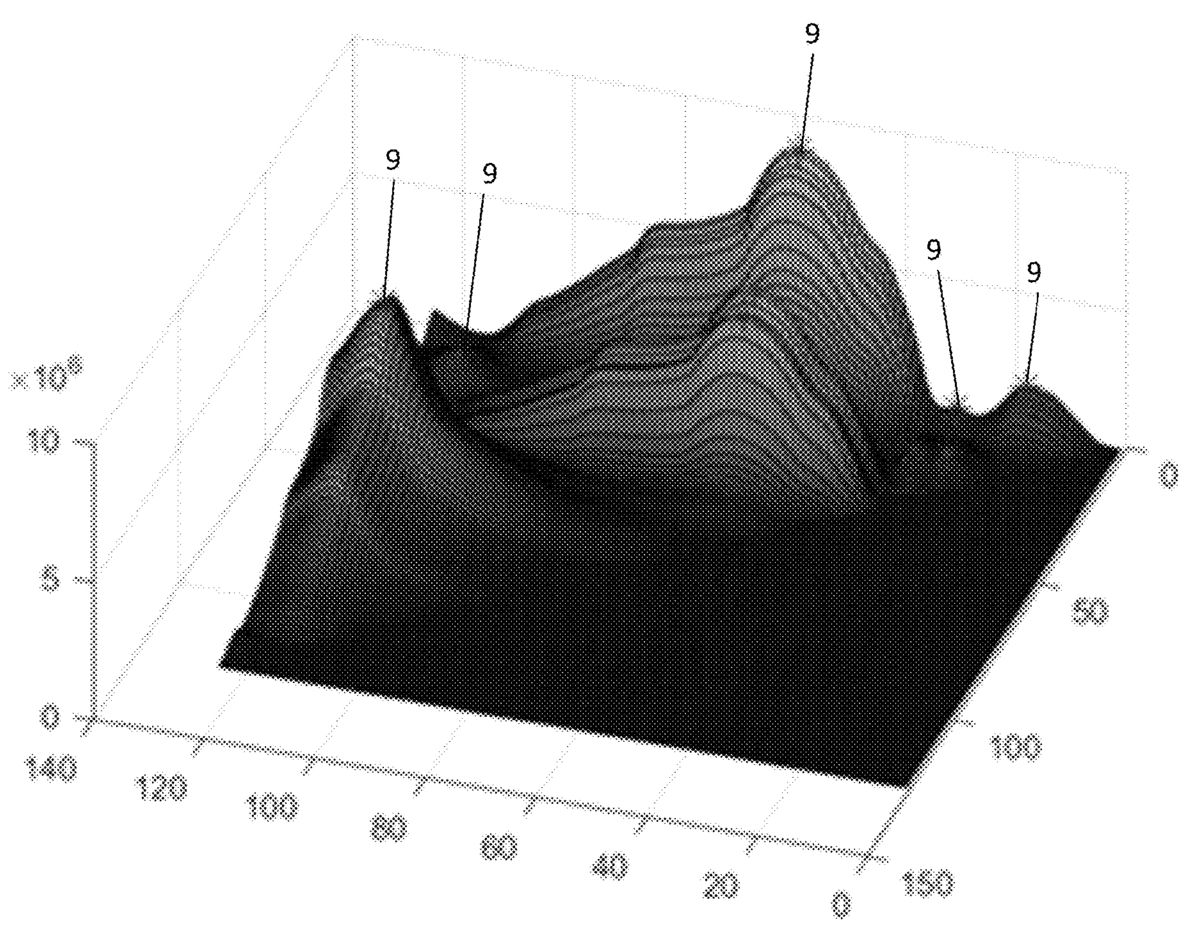
Figure 6C:
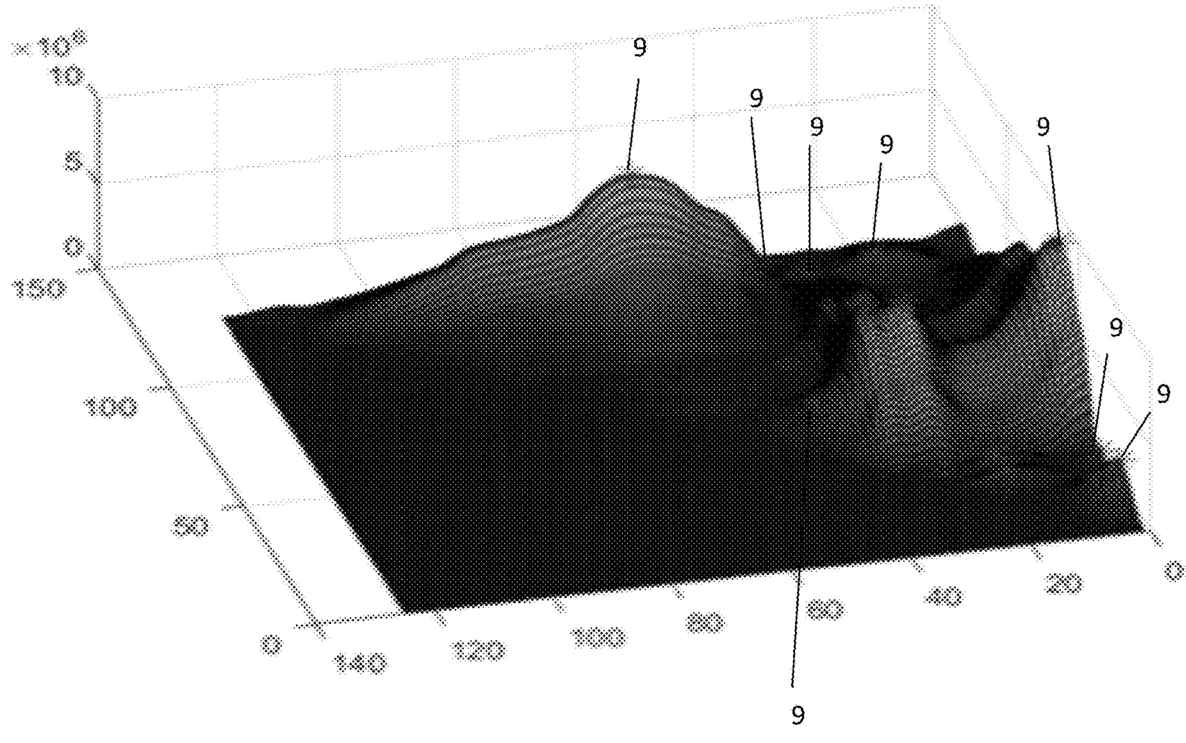

FIGS. 6*a-c* show the WPD plot for the VNIR data with the results of the peak finding algorithm added as asterisks 9. The terrain of this WPD matrix may be near-optimal for realizing the benefits of the SPM WPD band selection method. Prominent peaks rise above the floor of the surface plot to represent apparent differences between regions of high WPD values (and hence little redundancy between the associated bands) and low WPD values. The presently disclosed system and method successfully isolated the local maximum for each peak and identified several peaks near the floor of the surface plot with very low WPD values.

Figure 7:
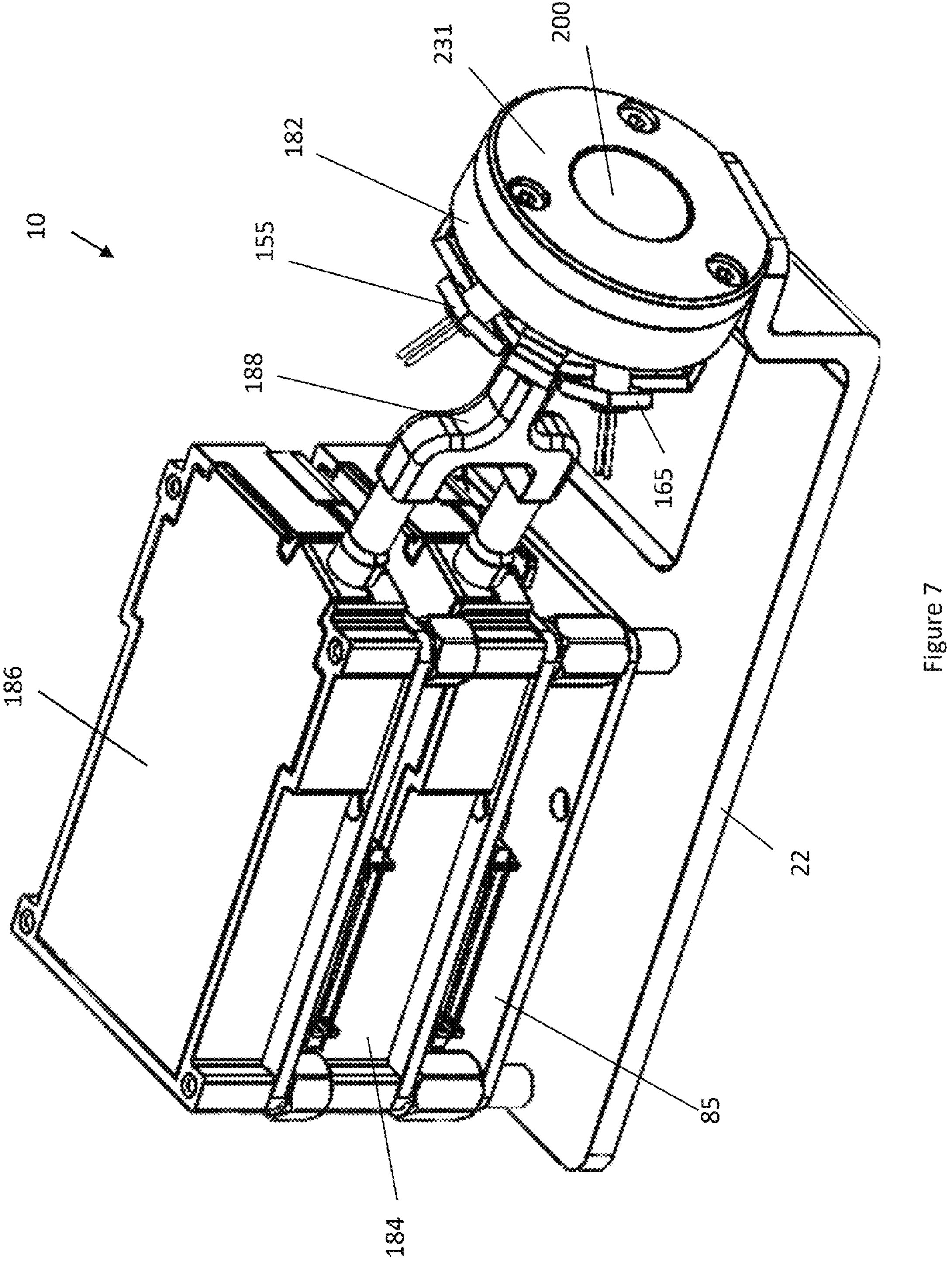
FIG. 7 depicts a device according to some embodiments presently disclosed.
Figure 8:
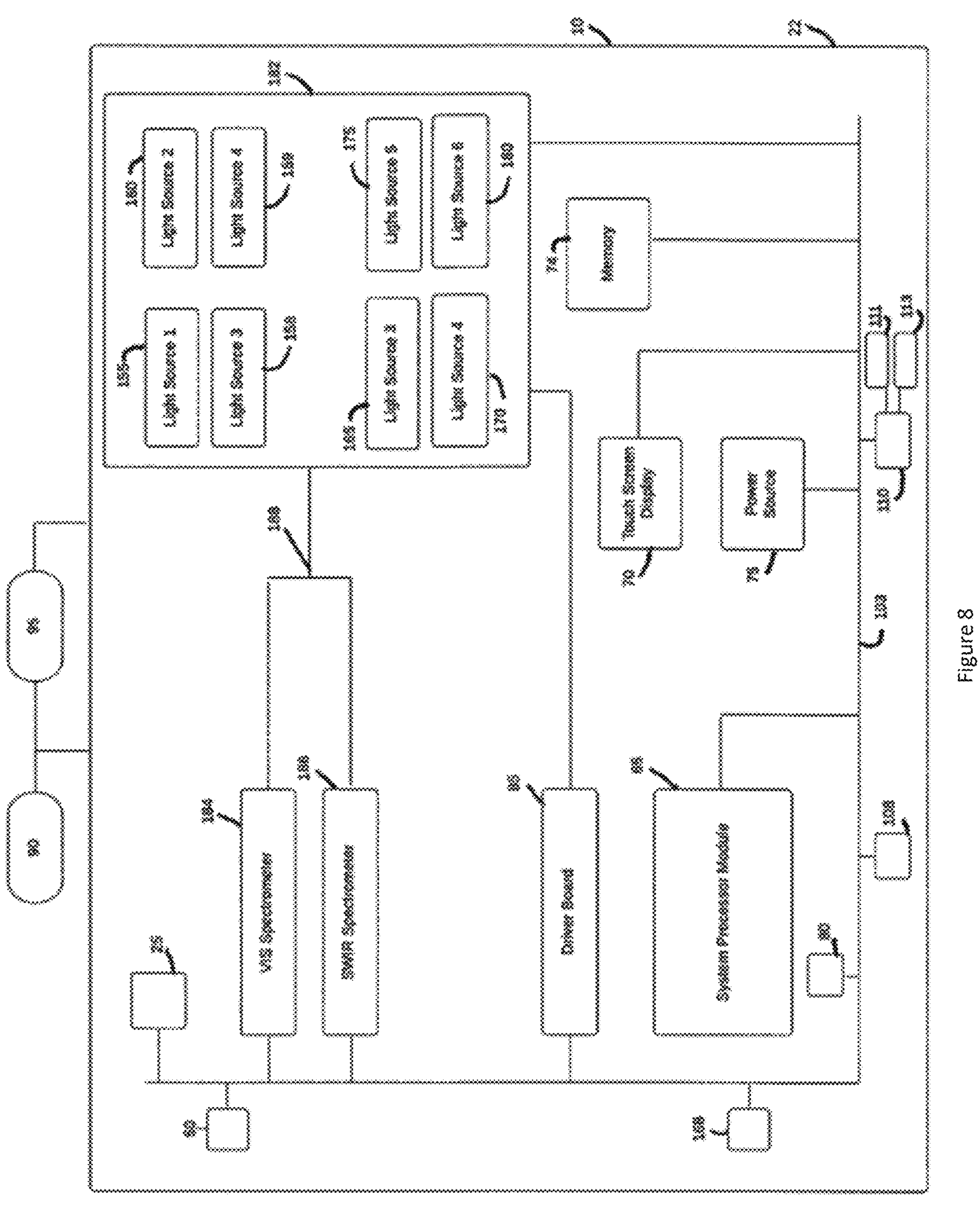
FIG. 8 depicts a block diagram of a device according to some embodiments presently disclosed.

Referring to FIG. 7, at least a portion of a device 10 is shown according to some embodiments presently disclosed. Referring to FIG. 8, a block diagram 20 is shown according to some embodiments presently disclosed. The block diagram 20 depicts some of the components of the device 10 and how they communicate with one another. According to some embodiments presently disclosed, the device 10 is a handheld device. According to some embodiments presently disclosed, the device 10 is part of non-invasive imaging system and method for assessing product(s).

The presently disclosed device 10 may be used to assess one or more products according to some embodiments presently disclosed. The products may be, for example, food related products, meat related products (i.e. beef, lamb, pork, poultry), seafood related products (i.e. fish, shellfish, seaweed), pharmaceutical related products, drug related products, construction related products, natural products, synthetic products, and/or other consumer related products.

According to some embodiments presently disclosed, an operator (i.e. user, technician) uses the device 10 to collect data on the one or more products.

According to some embodiments presently disclosed, the device 10 comprises a housing 22. According to some embodiments, the housing 22 of the device 10 comprises additional materials for ruggedization or to provide drop/impact resistance.

According to some embodiments presently disclosed, the device 10 comprises a memory 74 (which may comprise one or more computer readable storage mediums). The memory 74 may comprise high-speed random-access memory and/or non-volatile memory, such as one or more magnetic disk storage devices, flash memory devices, or other non-volatile solid-state memory devices. Access to memory 74 by other components of the device 10, such as one or more system processor modules 65 and a peripherals interface, may be controlled by a memory controller (not shown).

According to some embodiments presently disclosed, the device 10 comprises one or more system processor modules 65. The one or more system processor modules 65 run or execute various software programs and/or sets of instructions stored in memory 74 to perform various functions for the device 10 and to process data. The system processor module 65 may also comprise orientation sensors, motion sensors, global positioning systems, wireless communication systems such as WiFi or Bluetooth systems, cellular network communications systems such 4G, LTE or 5G or similar systems. The system processor module 65 may use these systems to communicate with a device server 90 or it may communicate with the device server via a wired connection through a peripheral interface. The system processor module 65 may also use these systems to communicate with other wireless devices such as cell phones, tablets, smart glasses, other inspection devices or other smart displays as well as RFID systems, barcode readers, fingerprint readers, etc. According to some embodiments, some or all of these components may be implemented on a single chip. According to some embodiments, some or all of these components may be implemented on separate chips.

According to some embodiments presently disclosed, the device 10 comprises an audio circuitry 110, a speaker 111, and a microphone 113. The audio circuitry 110, the speaker 111, and the microphone 113 provide an audio interface between a user (i.e. operator) and the device 10. The audio circuitry 110 receives audio data, converts the audio data to an electrical signal, and transmits the electrical signal to the speaker 111. The speaker 111 converts the electrical signal to human-audible sound waves. The audio circuitry 110 also receives electrical signals converted by the microphone 113 from sound waves. The audio circuitry 110 converts the electrical signal to audio data and transmits the audio data to one or more system processor modules 65 for processing. Audio data may be retrieved from and/or transmitted to memory 74. The audio circuitry 110 may also comprise a headset/speaker jack (not shown). The headset jack provides an interface between the audio circuitry 110 and removable audio input/output peripherals, such as speaker, output-only headphones and/or a headset with both output (e.g., a headphone for one or both ears) and input (e.g., a microphone).

According to some embodiments presently disclosed, the device 10 comprises a display 70. The display 70 may be a touch-sensitive display 70. The touch-sensitive display 70 is sometimes called a "touch screen" for convenience, and may also be known as or called a touch-sensitive display system. In one embodiment, the touch-sensitive touch screen 70 provides an input interface and an output interface between the device 10 and the user. The touch screen 70 is configured to implement virtual or soft buttons and one or more soft keyboards. A display controller receives and/or sends electrical signals from/to the touch screen 70. The touch screen 70 displays visual output to the user. The visual output may include graphics, text, icons, video, and any combination thereof (collectively termed "graphics"). In some embodiments, some or all of the visual output may correspond to user-interface objects, further details of which are described below.

The touch screen 70 has a touch-sensitive surface, sensor or set of sensors that accepts input from the user based on haptic and/or tactile contact. The touch screen 70 and the display controller (along with any associated modules and/or sets of instructions in memory 74) detect contact (and any movement or breaking of the contact) on the touch screen 70 and converts the detected contact into interaction with user-interface objects (e.g., one or more soft keys, icons, web pages or images) that are displayed on the touch screen. In one embodiment, a point of contact between a touch screen 70 and the user corresponds to a finger of the user.

The touch screen 70 may use LCD (liquid crystal display) technology, or LPD (light emitting polymer display) technology, although other display technologies may be used in other embodiments. The touch screen 70 and the display controller may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with the touch screen 70.

A touch-sensitive display in some embodiments of the touch screen 70 may be analogous to the multi-touch sensitive tablets described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety.

A touch-sensitive display in some embodiments of the touch screen 70 may be as described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

The touch screen 70 may have a resolution of 100 dpi. to 350 dpi. The user may make contact with the touch screen 70 using any suitable object or appendage, such as a stylus, a finger, and so forth. In some embodiments, the user interface is designed to work primarily with finger-based contacts and gestures, which are much less precise than stylus-based input due to the larger area of contact of a finger on the touch screen. In some embodiments, the device translates the rough finger-based input into a precise pointer/cursor position or command for performing the actions desired by the user.

In addition to the touch screen 70, the device 10 may comprise a touchpad (not shown) for activating or deactivating particular functions. The touchpad is a touch-sensitive area of the device that, unlike the touch screen, does not display visual output. The touchpad may be a touch-sensitive surface that is separate from the touch screen 70 or an extension of the touch-sensitive surface formed by the touch screen.

The one or more system processor modules 65 may be configured to communicate with the smart display 70 to provide information to the user during an inspection or to accept instructions from the operator during an inspection. According to some embodiments, the smart display 70 may be a passive device such as a touch screen display. According to some embodiments, the smart display 70 may be an active device with multiple processing and communication capabilities such as a smartphone or tablet. If the smart display 70 is an active device some of the system software functions may be shared between the one or more system processor modules 65 and the smartphone or tablet. According to some embodiments, the smart display 70 is a smartphone.

The device 10 may also comprise a radio frequency (RF) circuitry 108. The RF circuitry 108 may be configured to receive and transmit RF signals, also called electromagnetic signals. The RF circuitry 108 converts electrical signals to/from electromagnetic signals and communicates with communications networks and other communications devices via the electromagnetic signals. The RF circuitry 108 may include circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 108 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document. According to some embodiments, the radio frequency (RF) circuitry 108 allows the device 10 to communicate with a device server 90 and/or an external server 95.

The device 10 may also comprise a physical or virtual click wheel (not show) and/or one or more controls 80 as an input control device. The user may navigate among and interact with one or more graphical objects (henceforth referred to as icons) displayed in the screen 70 by rotating the click wheel or by moving a point of contact with the click wheel (e.g., where the amount of movement of the point of contact is measured by its angular displacement with respect to a center point of the click wheel) or by activating the one or more controls 80. The click wheel may also be used to select one or more of the displayed icons. For example, the user may press down on at least a portion of the click wheel or an associated button. User commands and navigation commands provided by the user via the click wheel may be processed by an input controller as well as one or more of the modules and/or sets of instructions in memory 74. For a virtual click wheel, the click wheel and click wheel controller may be part of the touch screen 70 and the display controller, respectively. For a virtual click wheel, the click wheel may be either an opaque or semitransparent object that appears and disappears on the touch screen display in response to user interaction with the device. In some embodiments, a virtual click wheel is displayed on the touch screen of a portable multifunction device and operated by user contact with the touch screen.

According to some embodiments presently disclosed, the device 10 comprises a power system 75. The power system 75 powers various components of the device 10. The power system 75 may comprise a power management system, one or more power sources (e.g., battery, alternating current (AC)), a recharging system, a power failure detection circuit, a power converter or inverter, a power status indicator (e.g., a light-emitting diode (LED)) and/or any other components associated with the generation, management and distribution of power in portable devices.

According to some embodiments presently disclosed, the device 10 comprises an optical sensor 25. The optical sensor 25 of the device 10 may be electrically coupled with an optical sensor controller. The optical sensor 25 may comprise charge-coupled device (CCD) or complementary metal-oxide semiconductor (CMOS) phototransistors. The optical sensor 25 receives light from the environment, projected through one or more lens, and converts the light to data representing an image. In conjunction with an imaging module (also called a camera module), the optical sensor 25 may capture visual media (i.e. still images or video). In some embodiments, the optical sensor 25 may be located on the front of the device 10, opposite the touch screen display 70 on the back of the device 10, so that the touch screen display 70 may be used as a viewfinder for either still and/or video image acquisition. In some embodiments, the optical sensor 25 may be located on the back of the device 10 to capture image(s) of the user. In some embodiments, one optical sensor 25 may be located on the back of the device 10 and another optical sensor 25 may be located on the front of the device 10. In some embodiments, the position of the optical sensor 25 may be changed by the user (e.g., by rotating the lens and the sensor in the device housing) so that a single optical sensor 25 may be used along with the touch screen display to capture still and/or video image.

According to some embodiments presently disclosed, the optical sensor 25 may comprise fluorescence imaging camera, 3D stereoscopic imaging camera, thermal imaging camera, or speckle imaging camera.

According to some embodiments presently disclosed, the optical sensor 25 may comprise triple band pass filter. The triple band pass filters are configured to cut off the NADH excitation wavelength to the optical sensor 25. According to some embodiments presently disclosed, the optical sensor 30 may comprise double band pass filter. The double band pass filters are configured to cut off the NADH/FAD excitation wavelength to the optical sensor 25.

According to some embodiments presently disclosed, the optical sensor 25 is a color optical sensor. According to some embodiments presently disclosed, the optical sensor 25, when imaging under ambient light, may act as a view finder for operators to position the system correctly prior to biomarker measurements and for conventional wound dimension measurements.

According to some embodiments presently disclosed, the device 10 comprises a range finder to calibrate the field of view at each image capture distance for comparing wound dimensions across different images and over time.

According to some embodiments presently disclosed, the device 10 may also comprise one or more accelerometers 168 as shown in FIG. 3. The accelerometer 168 may perform as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are which are incorporated herein by reference in their entirety. Information may be displayed on the touch screen display in a portrait view or a landscape view based on an analysis of data received from the one or more accelerometers 168.

According to some embodiments, the memory 74 may be configured to store one or more software components as described below.

The memory 74 may be configured to store an operating system. The operating system (e.g., Darwin, RTXC, LINUX, UNIX, OS X, WINDOWS, or an embedded operating system such as VxWorks) comprises various software components and/or drivers for controlling and managing general system tasks (e.g., memory management, storage device control, power management, etc.) and facilitates communication between various hardware and software components.

The memory 74 may be configured to store a system software. The system software may provide data storage for measurements and other information that are transferred from the device 10. The system software may provide system management functions for managing the creation of jobs and task lists that can be implemented using the device 10. The system software may be configured to manage data storage and creation of jobs and task lists for one or more devices 10 for an organization. The system software may comprise firmware software, analysis software, and user interface software.

The memory 74 may also be configured to store a communication module. The communication module facilitates communication with other devices over one or more external ports and also includes various software components for handling data received by the RF circuitry 108 and/or the external port. In one embodiment, the external port (e.g., Universal Serial Bus (USB), FIREWIRE, etc.) is configured for coupling directly to other devices or indirectly over a network (e.g., the Internet, wireless LAN, etc.).

The memory 74 may be configured to store a contact/motion module. The contact/motion module is configured to detect contact with the touch screen 70 (in conjunction with the display controller) and other touch sensitive devices (e.g., a touchpad or physical click wheel). The contact/motion module includes various software components for performing various operations related to detection of contact, such as determining if contact has occurred, determining if there is movement of the contact and tracking the movement across the touch screen 74, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). The contact/motion module and the display controller may also detect contact on a touchpad. The contact/motion module and the controller may further detect contact on a click wheel.

The memory 74 may be configured to store a graphics module. The graphics module comprises various known software components for rendering and displaying graphics on the touch screen 70, including components for changing the intensity of graphics that are displayed. As used herein, the term "graphics" includes any object that can be displayed to a user, including without limitation text, web pages, icons (such as user-interface objects including soft keys), digital images, videos, animations and the like.

The memory 74 may also be configured to store a text input module. The text input module, which may be a component of graphics module, provides soft keyboards for entering text in various applications that need text input.

The memory 74 may be configured to store a GPS module. The GPS module determines the location of the device and provides this information for use in various applications (e.g., to camera module as picture/video metadata).

The memory 74 may be configured to store applications. The applications may comprise one or more of the following modules (or sets of instructions), or a subset or superset thereof: a camera module for still and/or video images; an image management module; a video player module; and/or online video module.

The applications may comprise additional modules (or sets of instructions). For example, other applications that may be stored in memory 74 may include one or more of the following: a contacts module (sometimes called an address book or contact list); a telephone module; a video conferencing module; an e-mail client module; an instant messaging (IM) module; a browser module; a calendar module; search module; notes module; map module; word processing applications; JAVA-enabled applications; encryption; digital rights management; voice recognition; and/or voice replication.

The camera module (in conjunction with, for example, touch screen 70, display controller, optical sensor(s) 25, optical sensor controller, contact module, graphics module, and image management module) may be configured to capture still images or video (including a video stream) and store them into memory 74, modify characteristics of a still image or video, or delete a still image or video from memory 74.

The image management module (in conjunction with, for example, touch screen 70, display controller, contact module, graphics module, text input module, and camera module) may be configured to arrange, modify or otherwise manipulate, label, delete, present (e.g., in a digital slide show or album), and store still and/or video images.

The video player module (in conjunction with, for example, touch screen 70, display controller, contact module, graphics module, audio circuitry 110, and speaker 111) may be configured to display, present or otherwise play back videos (e.g., on the touch screen 70 or on an external, connected display via external port).

The online video module (in conjunction with, for example, touch screen 70, display system controller, contact module, graphics module, audio circuitry 110, speaker 111, RF circuitry 108) may be configured to allow the user to access, browse, receive (e.g., by streaming and/or download), play back (e.g., on the touch screen 70 or on an external, connected display via external port), upload and/or otherwise manage online videos in one or more file formats.

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. For example, video player module may be combined with another module into a single module. The memory 74 may store a subset of the modules and data structures identified above. Furthermore, memory 74 may store additional modules and data structures not described above.

The device 10 may be configured so as to allow operation of a predefined set of functions on the device be performed exclusively through a touch screen 70 and/or a touchpad. By using a touch screen and/or a touchpad as the primary input/control device for operation of the device 10, the number of physical input/control devices (such as push buttons, dials, and the like) on the device 10 may be reduced.

The predefined set of functions that may be performed exclusively through a touch screen and/or a touchpad may include navigation between user interfaces. In some embodiments, the touchpad, when touched by the user, navigates the device 10 to a main, home, or root menu from any user interface that may be displayed on the device 10.

The device 10 as shown in FIG. 8 may comprise more or fewer components than shown, may combine two or more components, or a may have a different configuration or arrangement of the components. The various components shown in FIG. 8 may be implemented in hardware, software or a combination of both hardware and software, including one or more signal processing and/or application specific integrated circuits.

Components shown in FIG. 8 may communicate over one or more communication buses or signal lines 103.

According to some embodiments presently disclosed, the device 10 comprises a motion sensor, orientation sensor, temperature sensor, distance sensor, and/or a plurality of light sources 155-180. According to some embodiments presently disclosed, the device 10 may also comprise hand controls 80 and/or an illumination driver 85.

According to some embodiments, the illumination driver 85 controls and provides suitable power to the light sources 155-180. The light sources 155-180 may be activated by the illumination driver 85 in response to one or more signals from the system processor module 65. The light sources 155-180 can be operated in continuous or pulsed illumination modes. The pulse mode facilitates background image capture to enhance detectability in brighter ambient light. The illumination driver 85 receives one or more signals from the system processor module 65 to turn the light sources 155-180 on and off. During fluorescence imaging modes some of the light sources 155-180 are turned on and off sequentially via one or more signals from the system processor module 65.

According to some embodiments, the light sources 155-180 may be lasers, light emitting diodes (LEDs), lamps, or other sources of illumination capable of providing the appropriate wavelengths for fluorescence excitation. According to some embodiments, some of the light sources 155-180 are high power LEDs in the wavelength range of UV and blue/violet. According to some embodiments, some of the light sources 155-180 provide illumination time for fluorescence imaging of between 1 msec to 200 msec for each excitation wavelength. The actual time of the exposure for either fluorescence imaging may be controlled by a system software algorithm which takes into account the task being performed, distance to the surface, illumination light energy, required energy for excitation, required energy for disinfection, and other factors to calculate the illumination and imaging times.

When the task being performed is fluorescence imaging the system sets the illumination time based on the amount of energy the illumination system provides under UV illumination and under blue violet illumination at a known distance that was determined by measurement during a system calibration process. The system software determines the amount of illumination required for detection of a desired contaminant, such as saliva or biological residues or bacteria, from prior knowledge extracted from experimental measurements with known samples.

According to some embodiments, the system processor module 65 comprises a computer on an integrated circuit with a Central Processing Unit (CPU) with machine learning model computation, multiple data input and output ports, and peripheral device interfaces with connection to various other components as shown in FIG. 8. The system processor module 65 may host the system software that guides inspections, analyzes data, and communicates with the user (i.e. operator) of the device 10 and one or more external servers 90, 95. The system processor module 65 may provide control of the light sources 155-180 for imaging. The system processor module 65 may manage the timing and synchronization of the light sources 155-180. The system processor module 65 may process the captured images to provide meaningful information to operators and for inspection records.

According to some embodiments, the distance sensor 50 comprises at least one Light Detection and Ranging (LIDAR) sensor and directed towards the field of view of the surface being examined. According to some embodiments, the angular acceptance of the LIDAR sensor can be adjusted programmatically to overlap a desired field of view of the camera systems.

The system processor module 65 may be configured to receive and interpret signals from the hand actuated controls 80 of the device 10. Hand actuated controls 80 can include momentary push button switches, on/off push button switches, or multi-axis push button controls that can be used to guide a cursor on the display 70.

According to some embodiments, the device server 90 comprises a computer system connected either wirelessly or by a secure wire or fiberoptic connection to the device 10. According to some embodiments, the device server 90 is a cloud server. The device server 90 may be configured to host the image and inspection history databases for one or more devices 10 and communicates with the system software on one or more devices 10. According to some embodiments, the device server 90 manages the communication of data and reports to and from one or more external servers 95.

According to some embodiments, the one or more external servers 95 may be customer servers or servers providing other data such as local environmental conditions or local disease prevalence. The device server 90 may also host web portals where users of the device 10 and or their managers can view inspection histories, incident reports, device status, inspection status, and where users can setup inspection task lists and perform other management and reporting functions regarding cleanliness status and completeness of the tasks for an inspection task list, multiple inspection task lists for multiple handheld devices or operators, of a facility, or of multiple facilities.

According to some embodiments presently disclosed, the system software is fully or partially stored in memory of the device server 90. According to some embodiments presently disclosed, the system software runs on the device server 90.

According to some embodiments presently disclosed, the system software may provide data storage for measurements and other information that are transferred from the device 10. The system software on the device server 90 may provide system management functions for managing the creation of jobs and task lists that can be implemented using the device 10. The system software on the device server 90 may be configured to manage data storage and creation of jobs and task lists for one or more devices 10 for an organization. For example, a company may have five devices 10 at different locations that are managed from a single device server 90. According to some embodiments, the device server 90 may also manage data storage and creation of jobs and task lists for multiple organizations with multiple devices 10.

According to some embodiments presently disclosed, the device server 90 is a cloud server wirelessly connected to one or more devices 10 and providing services to many organizations. The cloud device server 90 may comprise web portals that are accessible through the internet where users or managers can manage one or more devices 10. The system management software on the device server 90 may provide for the creation, storage, and retrieval of inspection and sanitation reports. The system management software on the device server 90 may provide for the creation of a risk index for each inspection task and for analysis of previous inspection and sanitation reports to analyze ongoing risk and apply an updated risk index for each inspection task. The system management software on the device server 90 may provide the ability to communicate with external sources of data. External sources of data can be at least one of an organization server, an institutional server, a server providing data from a government or regulatory body, a server providing data from a public or private source of environmental, health, epidemiological, weather, population, scheduling, transportation, etc. information. The management software on the device server 90 may also provide data to local, regional, national, or international agencies or regulatory bodies.

The device server 90 may communicate task management information and collect data via wired or wireless methods to the system software on the device 10. The system software can communicate reports and measurement data and device 10 system status to the device server 90. The system software may comprise firmware software, analysis software, and user interface software.

The user interface software provides information and control screens on the display 70 to guide a user (i.e. operator) through assessment of the product and task list. According to some embodiments, the user interface software displays options to the operator via the display 70 and accepts input from the operator via either the display 70 or the hand controls 80 on the smart display and/or accepts input from the operator via the smart display 70 and the hand controls 80 on the device. According to some embodiments, the user interface software provides for communication of inspection tasks, inspection status and inspection results to the device server 90.

The firmware software may be directly connected to and controls the hardware components of the device 10. The user interface software provides information to and interprets commands from the device 10 operator. The analysis software continuously analyzes sensor measurements, analyzes image data, and provides information to the operator to guide the analysis of the product.

According to some embodiments presently disclosed, the device 10 may be used to collect full-resolution reflectance and fluorescence images of a product being tested. According to some embodiments presently disclosed, the device 10 comprises visible and near-infrared (VNIR) hyperspectral imaging system. The light source for VNIR reflectance may be, for example, a 150 W quartz tungsten lamp. For fluorescence imaging, two UV line light sources may be used, each with, for example, four 10 W, 365 nm, light-emitting diodes (LEDs). Reflectance images, for example, in 125 bands within the 419-1007 nm spectral range (4.4 nm at FWHM) and fluorescence images, for example, in 60 bands within the 438-718 nm range (4.4 nm at FWHM) may be acquired using, for example, a 23 mm focal length lens, an imaging spectrograph, and a 14-bit electron-multiplying charge-coupled device.

According to some embodiments presently disclosed, the device 10 comprises a frontend assembly 182 (shown in FIGS. 7, 8 and 9*a-b*) that is optically coupled with a first spectrometer 184 and a second spectrometer 186. The device 10 comprises a Y-coupler 188 to optically couple the frontend assembly 182 with the spectrometers 184 and 186. The Y-couple 188 connects output optical fibers from the frontend assembly 182 to the spectrometers 184 and 186.

According to some embodiments presently disclosed, the spectrometers 184 and 186 measure the spectrum of light transmitted from the frontend assembly 182. According to some embodiments presently disclosed, the spectrometers 184 and 186 measure the amount of light transmitted by a product as a function of wavelength. According to some embodiments presently disclosed, the spectrometer 184 is a visible (VIS) spectrometer and the spectrometer 186 is a short-wave infrared (SWIR) spectrometer.

Figure 9A:
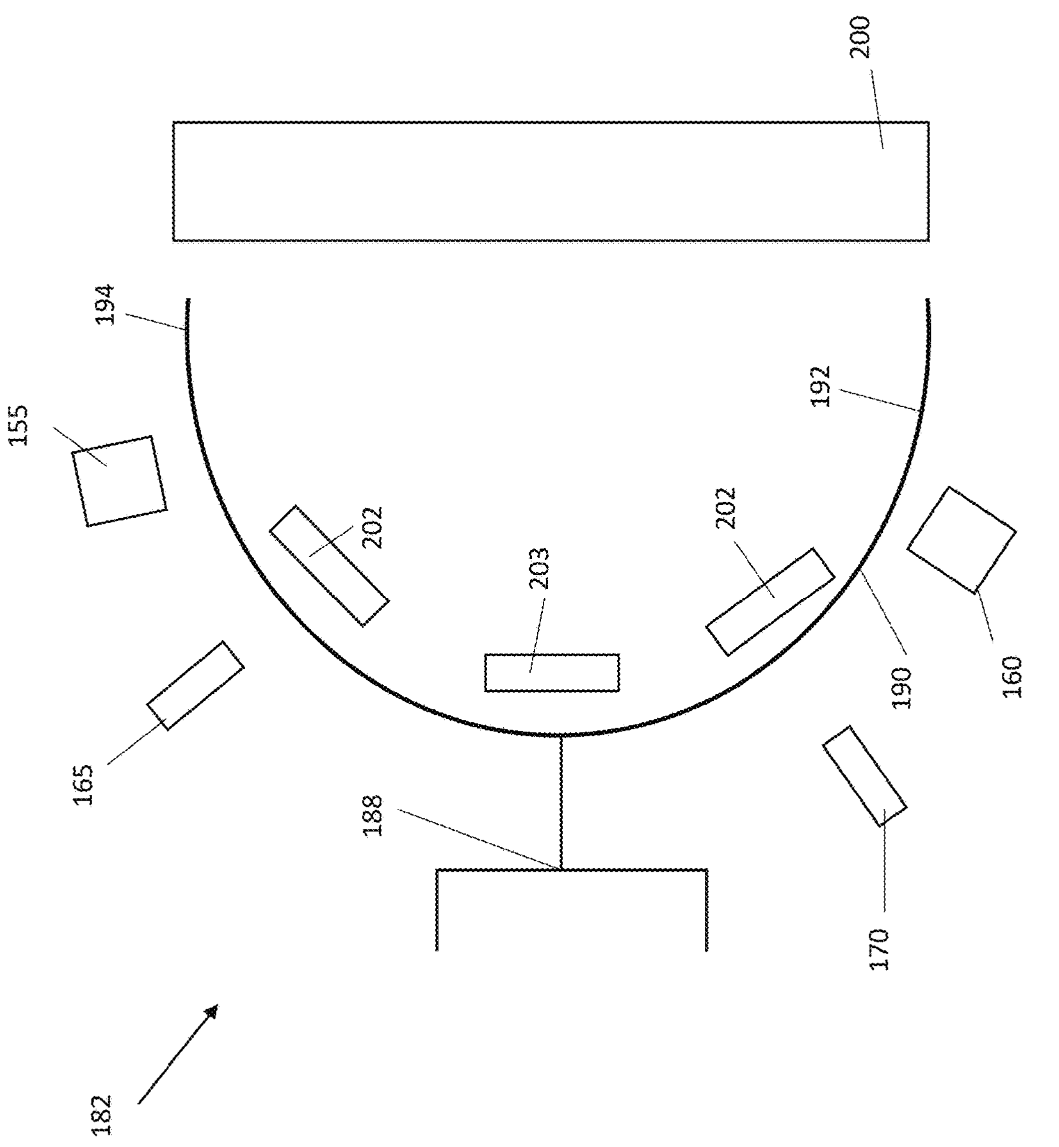
FIG. 9*a* depicts a cutaway side view of a frontend assembly according to some embodiments presently disclosed.
Figure 9B:
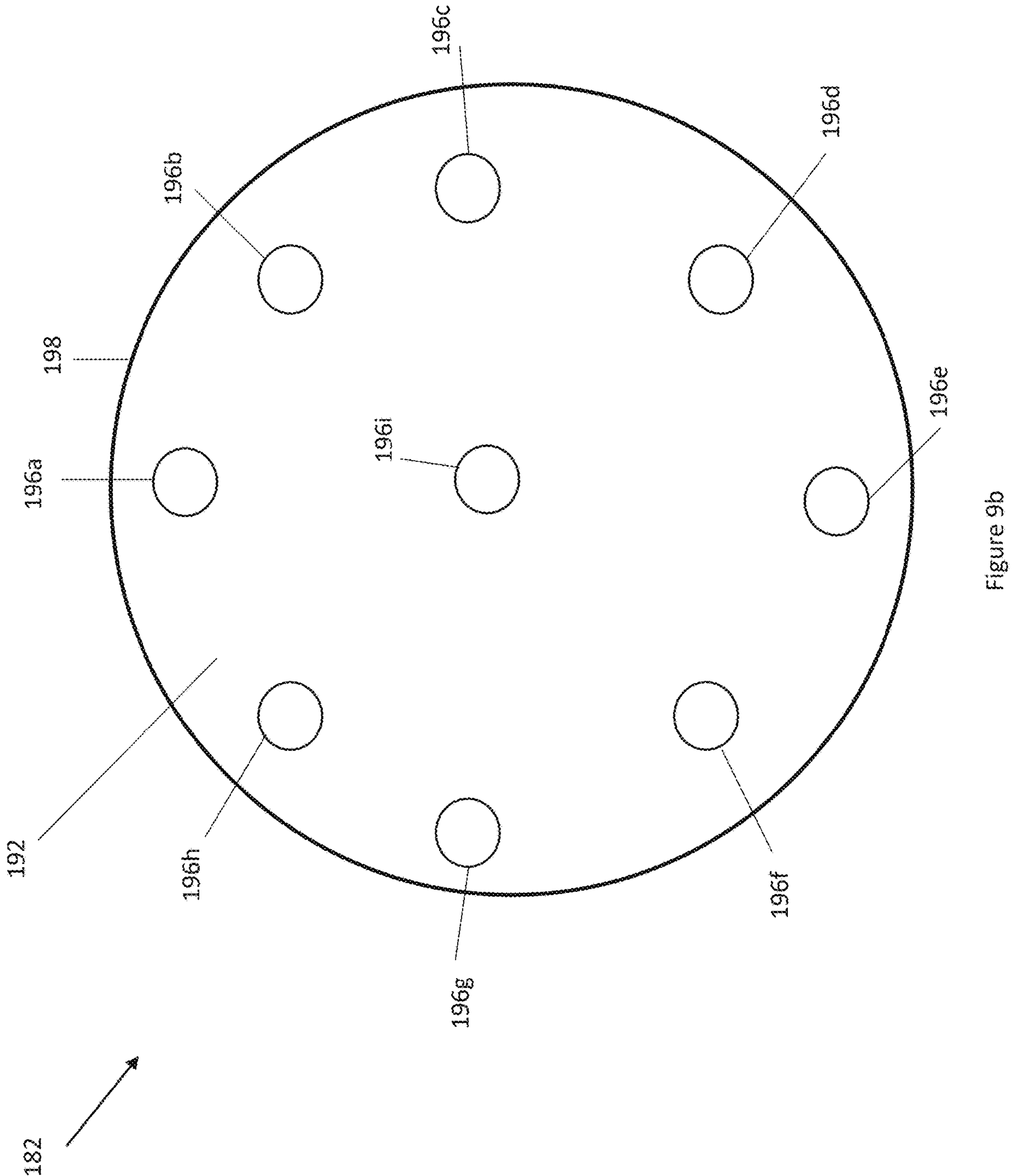
FIG. 9*b* depicts front view of a frontend assembly according to some embodiments presently disclosed.

Referring to FIG. 9*a*, a cut away side view of the frontend assembly 182 is shown according to some embodiments presently disclosed. Referring to FIG. 9*b*, front view of the frontend assembly 182 is shown according to some embodiments presently disclosed. According to some embodiments presently disclosed, the frontend end assembly 182 comprises housing 190 with one or more of the light sources 155-180 associated with the housing 190. According to some embodiments presently disclosed, the housing 190 comprises an inner surface 192 that is concave shaped. According to some embodiments presently disclosed, the housing 190 comprises an inner surface 192 that is hemispherical. According to some embodiments presently disclosed, the housing 190 comprises an outer surface 194 positioned opposite the inner surface 192. According to some embodiments presently disclosed, one or more of the light sources 155-180 are positioned along the outer surface 194 of the housing 190. According to some embodiments presently disclosed, the inner surface 192 comprises aluminum material. According to some embodiments presently disclosed, the housing 190 comprises aluminum material.

According to some embodiments presently disclosed, the light source 155 is a bulb. According to some embodiments presently disclosed, the light sources 155 and 158 are bulbs. According to some embodiments presently disclosed, the light sources 155, 158, and 159 are bulbs. According to some embodiments presently disclosed, the light sources 155, 158, 159, and 160 are bulbs.

According to some embodiments presently disclosed, the light source 155 is a tungsten bulb. According to some embodiments presently disclosed, the light sources 155 and 158 are tungsten bulbs. According to some embodiments presently disclosed, the light sources 155, 158, and 159 are tungsten bulbs. According to some embodiments presently disclosed, the light sources 155, 158, 159, and 160 are tungsten bulbs.

According to some embodiments presently disclosed, the housing 190 comprises a plurality of through apertures 196*a-h* configured to allow light from one or more light sources 155-180 to pass through the housing 190 towards a window 200 described below. According to some embodiments presently disclosed, the apertures 196*a-h* are positioned along the perimeter edge 198 of the housing 190.

According to some embodiments presently disclosed, the frontend end assembly 182 comprises a window 200 positioned in front of the inner surface 192. According to some embodiments presently disclosed, the window 200 positioned over the concave surface 192. According to some embodiments presently disclosed, the window 200 comprises antireflective coating on a surface facing the inner surface 192. According to some embodiments presently disclosed, the window 200 is sapphire window.

According to some embodiments presently disclosed, the light source 155 is positioned in line with the apertures 196*a* to allow light from the light source 155 to pass through the aperture 196*a* towards the window 200. Referring to FIG. 9*b*, according to some embodiments presently disclosed, the light source 155 is positioned in line with the aperture 196*a* located, for example, substantially at a 12 o'clock position along the perimeter of the housing 190.

According to some embodiments presently disclosed, the light sources 155 and 158 are positioned in line with the apertures 196*a* and 196*e* to allow light from the light sources 155 and 158 to pass through the apertures 196*a* and 196*e* towards the window 200. Referring to FIG. 9*b*, according to some embodiments presently disclosed, the light source 155 is positioned in line with the aperture 196*a* located, for example, substantially at a 12 o'clock position along the perimeter of the housing 190. According to some embodiments presently disclosed, the light source 158 is positioned opposite the light source 155 and in line with the aperture 196*e* located, for example, substantially at a 6 o'clock position along the perimeter of the housing 190.

According to some embodiments presently disclosed, the light sources 155, 158, and 159 are positioned in line with the apertures 196*a*, 196*c*, and 196*e* to allow light from the light sources 155, 158 and 159 to pass through the apertures 196*a*, 196*c*, and 196*e* towards the window 200. Referring to FIG. 9*b*, according to some embodiments presently disclosed, the light source 155 is positioned in line with the aperture 196*a* located, for example, substantially at a 12 o'clock position along the perimeter of the housing 190. According to some embodiments presently disclosed, the light source 158 is positioned opposite the light source 155 and in line with the aperture 196*e* located, for example, substantially at a 6 o'clock position along the perimeter of the housing 190. According to some embodiments presently disclosed, the light source 159 is positioned in line with the aperture 196*c* located, for example, substantially at a 3 o'clock position along the perimeter of the housing 190.

According to some embodiments presently disclosed, the light sources 155, 158, 159 and 160 are positioned in line with the apertures 196*a*, 196*c*, 196*e*, and 96*g* to allow light from the light sources 155, 158, 159 and 160 to pass through the apertures 196*a*, 196*c*, 196*e*, and 196*g* towards the window 200. Referring to FIG. 9*b*, according to some embodiments presently disclosed, the light source 155 is positioned in line with the aperture 196*a* located, for example, substantially at a 12 o'clock position along the perimeter of the housing 190. According to some embodiments presently disclosed, the light source 158 is positioned opposite the light source 155 and in line with the aperture 196*e* located, for example, substantially at a 6 o'clock position along the perimeter of the housing 190. According to some embodiments presently disclosed, the light source 159 is positioned in line with the aperture 196*c* located, for example, substantially at a 3 o'clock position along the perimeter of the housing 190. According to some embodiments presently disclosed, the light source 160 is positioned opposite the light source 159 and in line with the aperture 196*g* located, for example, substantially at a 9 o'clock position along the perimeter of the housing 190.

According to some embodiments presently disclosed, the light source 165 is a light emitting diode (LED). According to some embodiments presently disclosed, the light sources 165 and 170 are LEDs. According to some embodiments presently disclosed, the light sources 165, 170, and 175 are LEDs. According to some embodiments presently disclosed, the light sources 165, 170, 175, and 180 are LEDs.

According to some embodiments presently disclosed, the light source 165 operates at a first wavelengths. According to some embodiments presently disclosed, the light source 170 operates at the first wavelengths. According to some embodiments presently disclosed, the light source 175 operates at a second wavelengths. According to some embodiments presently disclosed, the light source 180 operates at the second wavelengths. According to some embodiments presently disclosed, the first wavelength is, for example, 365 nm, 395 nm or 405 nm. According to some embodiments presently disclosed, the second wavelength is, for example, 365 nm, 395 nm or 405 nm.

According to some embodiments presently disclosed, the light source 165 is a multimodal light source that operates at least at two different wavelengths. According to some embodiments presently disclosed, the light source 165 operates at, for example, nm and 395 nm; or 365 nm and 405 nm; or 395 nm and 405 nm.

According to some embodiments presently disclosed, the light source 170 is a multimodal light source that operates at least at two different wavelengths. According to some embodiments presently disclosed, the light source 170 operates at, for example, nm and 395 nm; or 365 nm and 405 nm; or 395 nm and 405 nm.

According to some embodiments presently disclosed, the light source 175 is a multimodal light source that operates at least at two different wavelengths. According to some embodiments presently disclosed, the light source 175 operates at, for example, nm and 395 nm; or 365 nm and 405 nm; or 395 nm and 405 nm.

According to some embodiments presently disclosed, the light source 180 is a multimodal light source that operates at least at two different wavelengths. According to some embodiments presently disclosed, the light source 180 operates at, for example, nm and 395 nm; or 365 nm and 405 nm; or 395 nm and 405 nm.

According to some embodiments presently disclosed, the light source 165 is positioned in line with the apertures 196*b* to allow light from the light source 165 to pass through the aperture 196*b* towards the window 200. Referring to FIG. 9*b*, according to some embodiments presently disclosed, the light source 165 is positioned in line with the aperture 196*b* located, for example, between a 12 o'clock position and a 3 o'clock position along the perimeter of the housing 190.

According to some embodiments presently disclosed, the light sources 165 and 170 are positioned in line with the apertures 196*b* and 196*f* to allow light from the light sources 165 and 170 to pass through the apertures 196*b* and 196*f* towards the window 200. Referring to FIG. 9*b*, according to some embodiments presently disclosed, the light source 165 is positioned in line with the aperture 196*b* located, for example, between a 12 o'clock position and a 3 o'clock position along the perimeter of the housing 190. According to some embodiments presently disclosed, the light source 170 is positioned opposite the light source 165 and in line with the aperture 196*f* located, for example, between a 6 o'clock position and a 9 o'clock position along the perimeter of the housing 190.

According to some embodiments presently disclosed, the light sources 165, 170, and 175 are positioned in line with the apertures 196*b*, 196*f* and 196*h* to allow light from the light sources 165, 170 and 175 to pass through the apertures 196*b*, 196*f* and 196*h* towards the window 200. Referring to FIG. 9*b*, according to some embodiments presently disclosed, the light source 165 is positioned in line with the aperture 196*b* located, for example, between a 12 o'clock position and a 3 o'clock position along the perimeter of the housing 190. According to some embodiments presently disclosed, the light source 170 is positioned opposite the light source 165 and in line with the aperture 196*f* located, for example, between a 6 o'clock position and a 9 o'clock position along the perimeter of the housing 190. According to some embodiments presently disclosed, the light source 175 is positioned in line with the aperture 196*h* located, for example, between a 9 o'clock position and a 12 o'clock position along the perimeter of the housing 190.

According to some embodiments presently disclosed, the light sources 165, 170, 175 and 180 are positioned in line with the apertures 196*b*, 196*d*, 196*f* and 196*h* to allow light from the light sources 165, 170, 175 and 180 to pass through the apertures 196*b*, 196*d*, 196*f*, and 196*h* towards the window 200. Referring to FIG. 9*b*, according to some embodiments presently disclosed, the light source 165 is positioned in line with the aperture 196*b* located, for example, between a 12 o'clock position and a 3 o'clock position along the perimeter of the housing 190. According to some embodiments presently disclosed, the light source 170 is positioned opposite the light source 165 and in line with the aperture 196*f* located, for example, between a 6 o'clock position and a 9 o'clock position along the perimeter of the housing 190. According to some embodiments presently disclosed, the light source 175 is positioned in line with the aperture 196*h* located, for example, between a 9 o'clock position and a 12 o'clock position along the perimeter of the housing 190. According to some embodiments presently disclosed, the light source 180 is positioned opposite the light source 175 and in line with the aperture 196*d* located, for example, between a 3 o'clock position and a 6 o'clock position along the perimeter of the housing 190.

According to some embodiments presently disclosed, the frontend assembly 182 comprises one or more optical filters 202 positioned between the window 200 and the light sources 165, 170, 175, and/or 180. According to some embodiments presently disclosed, the one or more optical filters 202 are band pass filters or short pass filters. According to some embodiments presently disclosed, the one or more optical filters 202 remove emission tail generated by the light sources 165, 170, 175, and/or 180. According to some embodiments presently disclosed, the one or more optical filters 202 are thin film filter.

According to some embodiments presently disclosed, the device 10 is configured to operate in a reflectance imaging mode. According to some embodiments presently disclosed, the device 10 performs a reflectance analysis (i.e. reflectance test) when operating in the reflectance imaging mode.

Figure 10:
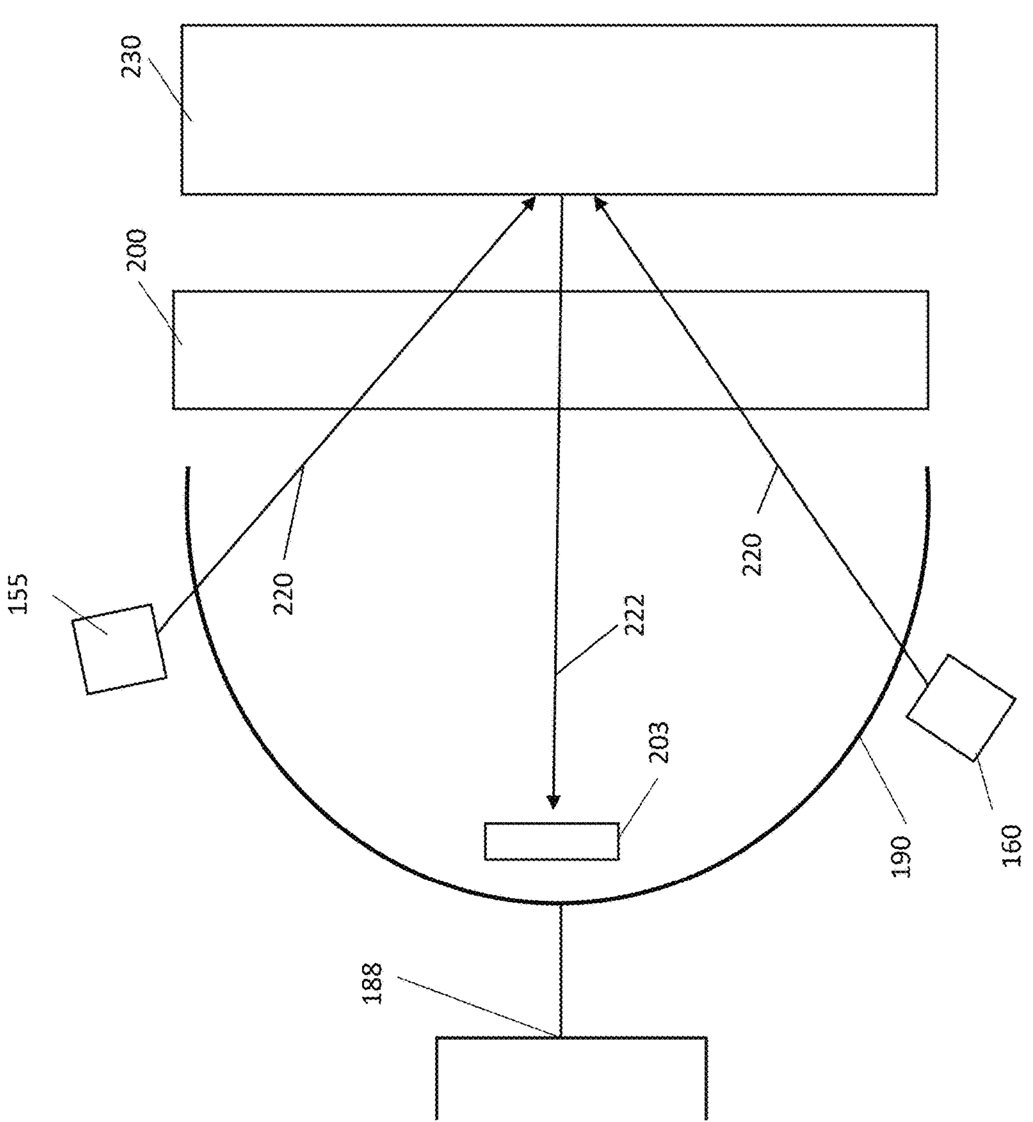
FIG. 10 depicts another cutaway side view of a frontend assembly according to some embodiments presently disclosed.

According to some embodiments presently disclosed, the device 10 performs a reflectance analysis (i.e. reflectance test) as shown in FIG. 10. A light 220 from at least light source 155 passes through the aperture 196*a* and the window 200 until it hits the product 230 being tested. Due to material properties of the product 230, at least some of the light 220's wavelengths will be absorbed or reflected by the product 230. According to some embodiments presently disclosed, at least a portion of a light 222 reflected by the product 230 is directed towards the y-coupler 188 through the window 200 and a through aperture 196*i*. According to some embodiments presently disclosed, the light 222 is a portion of the light 220 that has been reflected by the product 230 and spectrally modified and/or diffused by the product 230. According to some embodiments presently disclosed, the aperture 196*i* is positioned at the center of the inner surface 192. According to some embodiments presently disclosed, at least a portion of the light 222 will be directed by the y-coupler 188 to the spectrometers 184 and 186 for processing. According to some embodiments presently disclosed, at least a portion of the light 222 will be directed by the y-coupler 188 to the spectrometer 184 for processing. According to some embodiments presently disclosed, at least a portion of the light 222 will be directed by the y-coupler 188 to the spectrometer 186 for processing.

According to some embodiments presently disclosed, the light 220 is generated by the light source 155 and the light source 158. According to some embodiments presently disclosed, the light 220 is generated by the light source 159 and the light source 160. According to some embodiments presently disclosed, the light 220 is generated by the light source 155, the light source 158, the light source 159, and/or the light source 160. According to some embodiments presently disclosed, the light 220 is generated by activating any combinations of the light source 155, 158, 159, 160.

According to some embodiments presently disclosed, the device 10 is configured to operate in a first fluorescence imaging mode. According to some embodiments presently disclosed, the device 10 performs a first fluorescence analysis (i.e. first fluorescence test) when operating in the first fluorescence imaging mode.

Figure 11:
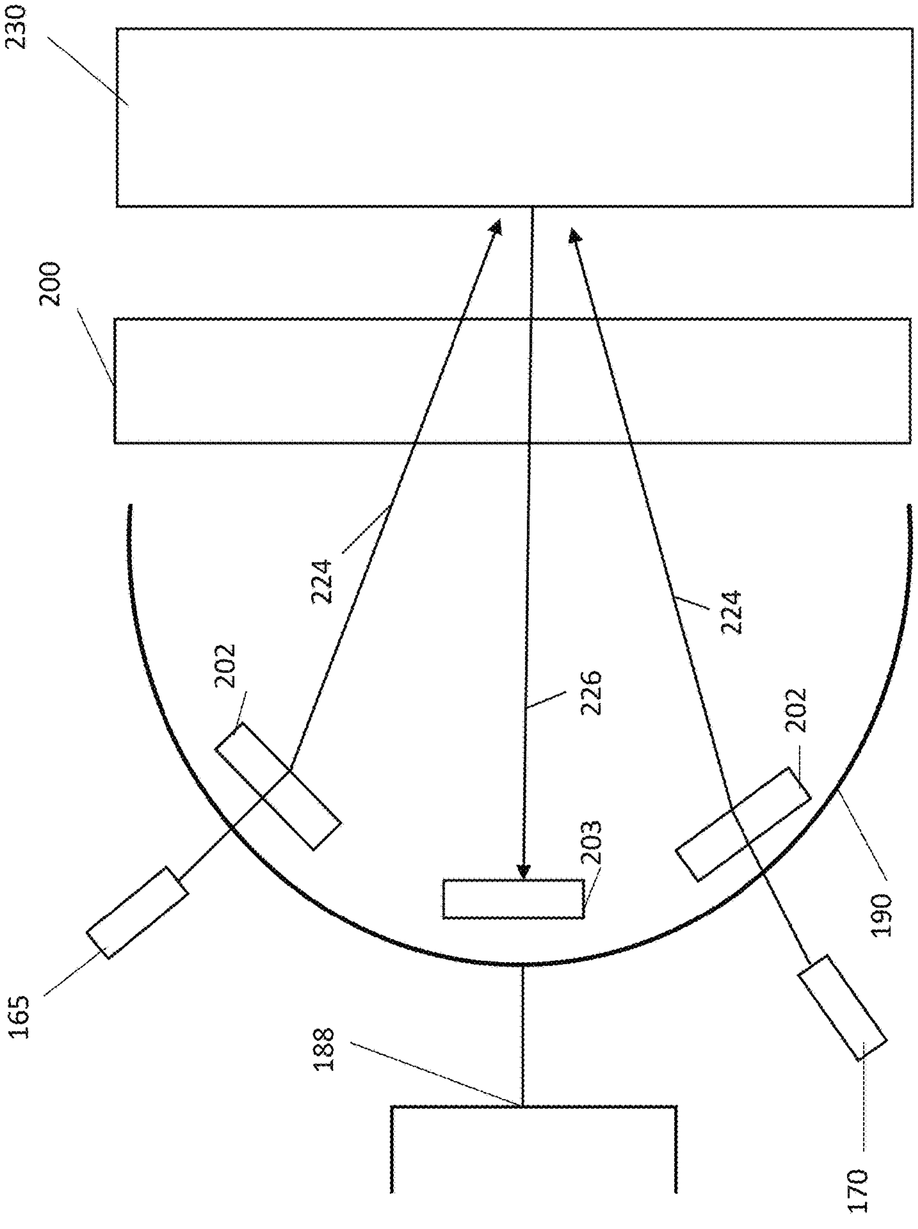
FIG. 11 depicts another cutaway side view of a frontend assembly according to some embodiments presently disclosed.

According to some embodiments presently disclosed, the device 10 performs a first fluorescence analysis (i.e. first fluorescence test) as shown in FIG. 11. A light 224 from at least light source 165 passes through the aperture 196*b* and the window 200 until it hits the product 230 being tested. Due to material properties of the product 230, at least some of the light 224's wavelengths will be absorbed or reflected by the product 230. According to some embodiments presently disclosed, at least a portion of a light 226 reflected by the product 230 is directed towards the y-coupler 188 through the window and the through aperture 196*i*. According to some embodiments presently disclosed, the light 226 is a portion of the light 224 that has been reflected by the product 230. According to some embodiments presently disclosed, at least a portion of the light 226 will be directed by the y-coupler 188 to the spectrometer 184 for processing. According to some embodiments presently disclosed, at least a portion of the light 226 will be directed by the y-coupler 188 to the spectrometer 186 for processing. According to some embodiments presently disclosed, at least a portion of the light 226 will be directed by the y-coupler 188 to the spectrometer 184 and the spectrometer 186 for processing.

According to some embodiments presently disclosed, the light 224 is generated by the light source 165 and the light source 170. According to some embodiments presently disclosed, the light 224 is generated by the light source 175 and the light source 180. According to some embodiments presently disclosed, the light 224 is generated by the light source 165, the light source 170, the light source 175, and/or the light source 180. According to some embodiments presently disclosed, the light 224 is generated by activating any combinations of the light source 165, 170, 175, 180. According to some embodiments presently disclosed, the light 224 is at a first wavelength. According to some embodiments presently disclosed, the light 224 is at a wavelength of 365 nm. According to some embodiments presently disclosed, the light 224 is at a wavelength of 395 nm. According to some embodiments presently disclosed, the light 224 is at a wavelength of 405 nm.

According to some embodiments presently disclosed, the device 10 is configured to operate in a second fluorescence imaging mode. According to some embodiments presently disclosed, the device 10 performs a second fluorescence analysis (i.e. first fluorescence test) when operating in the second fluorescence imaging mode.

Figure 12:
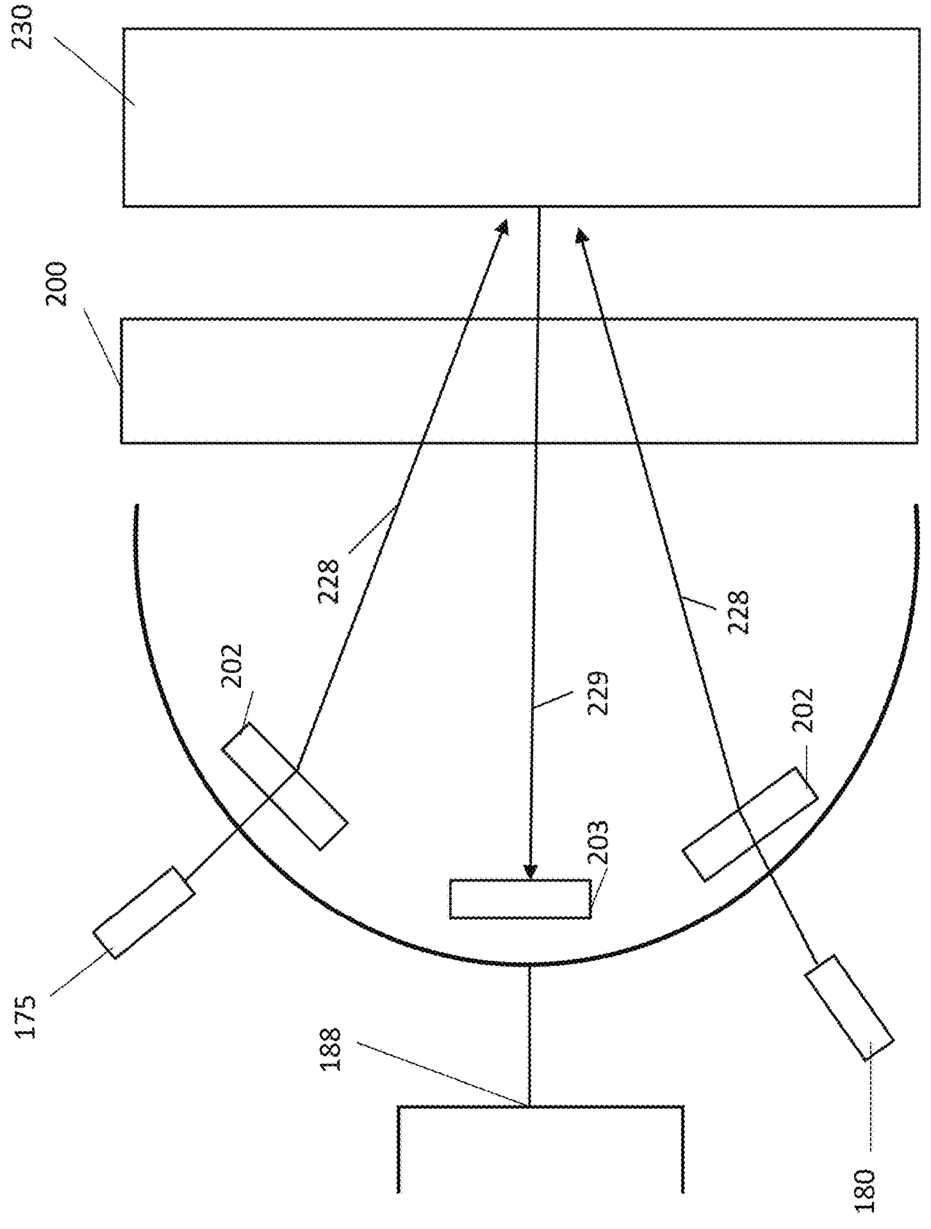
FIG. 12 depicts another cutaway side view of a frontend assembly according to some embodiments presently disclosed.

According to some embodiments presently disclosed, the device 10 performs a second fluorescence analysis (i.e. second fluorescence test) as shown in FIG. 12. A light 228 from at least light source 175 passes through the aperture 196*h* and the window 200 until it hits the product 230 being tested. Due to material properties of the product 230, at least some of the light 228's wavelengths will be absorbed or reflected by the product 230. According to some embodiments presently disclosed, at least a portion of a light 229 reflected by the product 230 is directed towards the y-coupler 188 through the window 200 and the through aperture 196*i*. According to some embodiments presently disclosed, the light 229 is a portion of the light 228 that has been reflected by the product 230. According to some embodiments presently disclosed, at least a portion of the light 229 will be directed by the y-coupler 188 to the spectrometer 184 for processing. According to some embodiments presently disclosed, at least a portion of the light 229 will be directed by the y-coupler 188 to the spectrometer 186 for processing. According to some embodiments presently disclosed, at least a portion of the light 229 will be directed by the y-coupler 188 to the spectrometer 184 and the spectrometer 186 for processing.

According to some embodiments presently disclosed, the light 228 is generated by the light source 175 and the light source 180. According to some embodiments presently disclosed, the light 228 is generated by the light source 165 and the light source 170. According to some embodiments presently disclosed, the light 228 is generated by the light source 165, the light source 170, the light source 175, and/or the light source 180. According to some embodiments presently disclosed, the light 228 is generated by activating any combinations of the light source 165, 170, 175, 180. According to some embodiments presently disclosed, the light 228 is at a second wavelength. According to some embodiments presently disclosed, the first wavelength used in the first fluorescence test is different from the second wavelength using in the second fluorescence test. According to some embodiments presently disclosed, the light 224 is at a wavelength of 365 nm. According to some embodiments presently disclosed, the light 224 is at a wavelength of 395 nm. According to some embodiments presently disclosed, the light 224 is at a wavelength of 405 nm.

According to some embodiments presently disclosed, the device 10 performs the first fluorescence test and the second fluorescence test using same light sources operating at first wavelength for the first fluorescence test and operating at a second wavelength for the second fluorescence test.

According to some embodiments presently disclosed, the frontend assembly 182 comprises an optical filter 203 positioned between the window 200 and the aperture 196*i*. According to some embodiments presently disclosed, the optical filter 203 is a long pass filter.

According to some embodiments, the frontend assembly 182 comprises a spacer ring 231 (shown in FIG. 7) to prevent products 230 from touching the window 200. According to some embodiments, the product 230 may be positioned 2 mm-3 mm away from the window 200.

According to some embodiments presently disclosed, the device 10 performs three modes. The three modes are three spectroscopy modes. The three spectroscopy modes are reflectance imaging mode, first fluorescence imaging mode, and second fluorescence imaging mode as described above.

Figure 13:
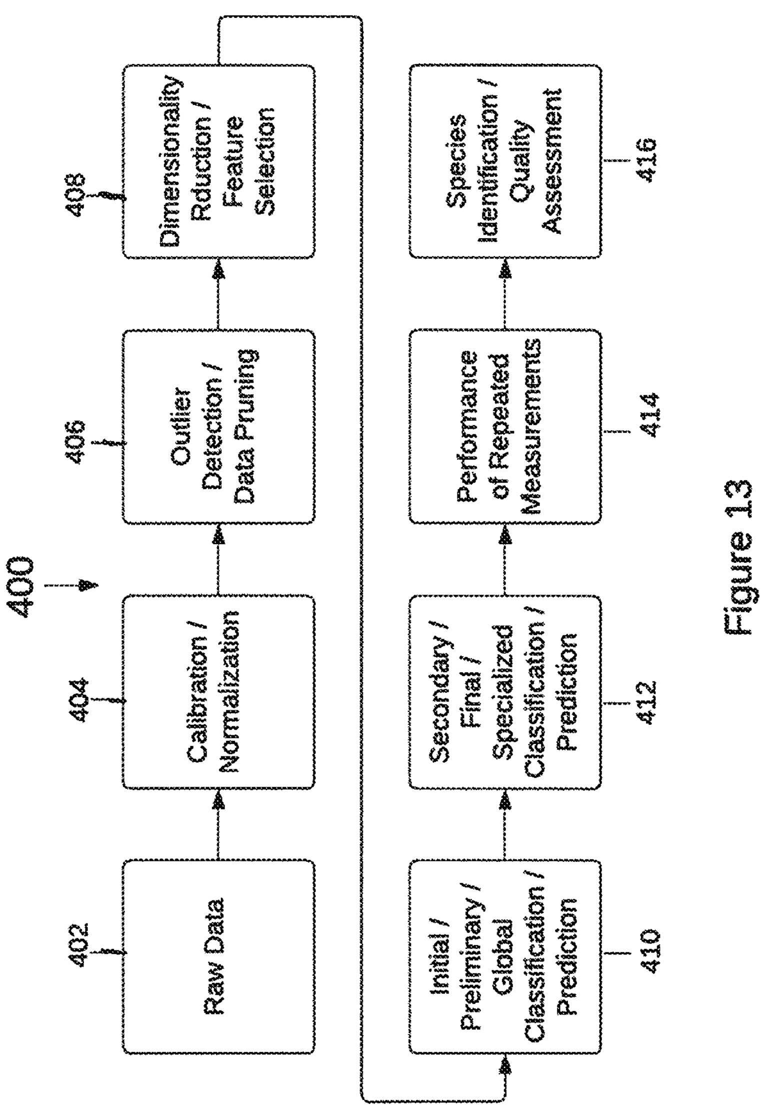
FIG. 13 depicts a method according to some embodiments presently disclosed.

Referring to FIG. 13, a method 400 is shown according to some embodiments presently disclosed. At 402, the device 10 generates raw data for the product 230. The raw data may also comprise dark current data, and/or white reference, and/or spectral data for the tested product 230, and/or exposure times data. The spectral data for the product 230 is based at least on data generated by the first fluorescence test, the second fluorescence test and the reflectance test.

At 404, reflectance data of the product 230 may be calibrated/adjusted by subtracting the dark current and by dividing by the white reference spectra. In order to be able to fuse the fluorescence mode with the reflectance modes the fluorescence data may be normalized using different methods such as, for example, standard normal variate (SNV).

At 406, the outliers may be detected using data quality strategies such as, for example, based on the criterion that they exceed mean+/− twice the standard deviation of all the measurements of the product 230.

At 408, dimensionality reduction may be used to remove redundant information and reducing data from higher to lower level dimensions. Feature selection may also be performed to understand which wavelength bands are more important. More details may be found in an article by Karl Pearson F.R.S., 1901. LIII. On lines and planes of closest fit to systems of points in space. The London, Edinburgh, and Dublin Philosophical Magazine and Journal of Science, 2(11), pp. 559-572, which is incorporated herein by reference in its entirety. More details may also be found in an article by Nicolas Meyer, Myriam Maumy-Bertrand, Frederic Bertrand, 2010. Comparaison de la regression PLS et de la regression logistique PLS: application aux donnees d'allelotypage. Journal de la Societe Francaise de Statistique, 151(2), pp. 1-18, which is incorporated herein by reference in its entirety.

At 410, single mode initial/preliminary/global classification may be performed for each of the three spectroscopy modes to obtain their initial predictions. According to some embodiments, the three spectroscopy modes are based at least on data generated by the first fluorescence test, the second fluorescence test and the reflectance test. The data from all three spectroscopy modes may be fused in two ways: decision level fusion and feature level fusion as shown in FIGS. 16-19 described below.

At 412, secondary/final/specialized classification methods such as, for example, sub-model analysis, ensemble stacking, decision-making system such as, for example, voting, weighted sum or other methods may be implemented to improve the accuracy. The sub-model technique improves the accuracies of low performing species, while ensemble stacking increases the overall accuracy by using multiple complimentary classification models. According to some embodiments, the combination of fusion, stacking and submodel may be implemented on the quality adulteration and traceability (QAT) device chip. At 414, the performance of the models may be improved by measuring multiple points on the product 230 and increase in performance may be evaluated. At 416, the product 230 is identified.

Figure 14:
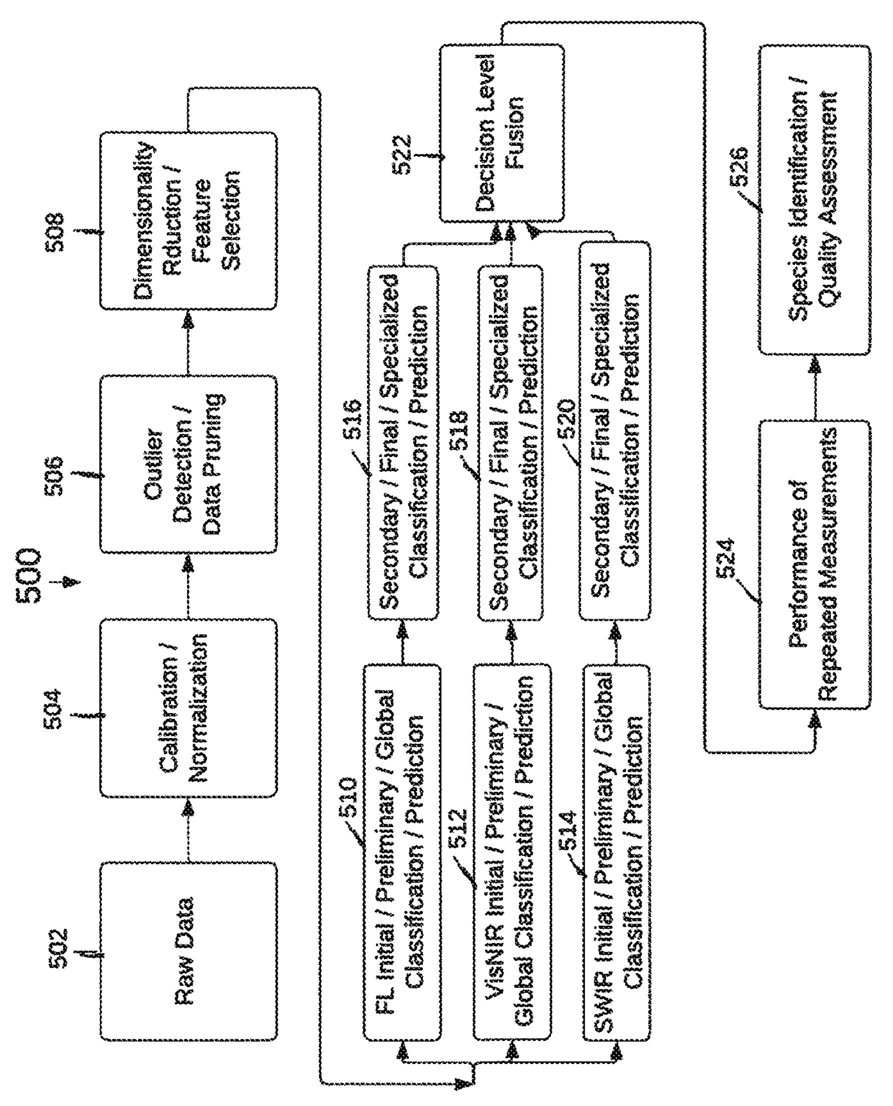
FIG. 14 depicts another method according to some embodiments presently disclosed.

Referring to FIG. 14, a method 500 is shown according to some embodiments presently disclosed. According to some embodiments, the method 500 provides Artificial Intelligence (AI)/Machine learning (ML) for decision level fusion. At 502, the device 10 generates raw data for the product 230. The raw data may also comprise dark current data, and/or white reference, and/or spectral data for the tested product 230, and/or exposure times data. The spectral data for the product 230 is based at least on data generated by the first fluorescence test, the second fluorescence test and the reflectance test.

At 504, reflectance data of the product 230 may be calibrated/adjusted by subtracting the dark current and by dividing by the white reference spectra. In order to be able to fuse the fluorescence mode with the reflectance modes the fluorescence data may be normalized using different methods such as, for example, standard normal variate (SNV).

At 506, the outliers may be detected using data quality strategies such as, for example, based on the criterion that they exceed mean+/− twice the standard deviation of all the measurements of the product 230.

At 508, dimensionality reduction may be used to remove redundant information and reducing data from higher to lower level dimensions. Feature selection may also be performed to understand which wavelength bands are more important.

At 510, initial/preliminary/global single mode classification may be performed for fluorescence classification to obtain its performances. At 516, a secondary/final/specialized classification such as, for example, a sub-model analysis and/or ensemble stacking may be implemented on data from 510 to improve the accuracy of low performing species.

At 512, initial/preliminary/global single mode classification may be performed for reflectance classification. At 518, a secondary/final/specialized classification such as, for example, a sub-model analysis and/or ensemble stacking may be implemented on data from 512 to improve the accuracy of low performing species.

At 514, initial/preliminary/global single mode classification may be performed for reflectance classification. At 520, a secondary/final/specialized classification such as, for example, a sub-model analysis and/or ensemble stacking may be implemented on data from 514 to improve the accuracy of low performing species.

At 522, the data from 516, 518 and 520 may be fused in decision level fusion. In decision level fusion, the predictions of the three single-mode models are entered into a decision mechanism such as, for example, majority vote, weighted sum or any other method where the final prediction will be the specie/freshness that most modes predict.

At 524, multiple measurements are taken from the sample for example the fillet to increase the amount of data which increases the chance of correct prediction. According to some embodiments, combination of fusion, stacking and sub-model may be implemented on the quality adulteration and traceability (QAT) device chip. The improvement in the performance of the models may be evaluated by increasing the number of measured points. At 526, the product 230 is identified.

Figure 15:
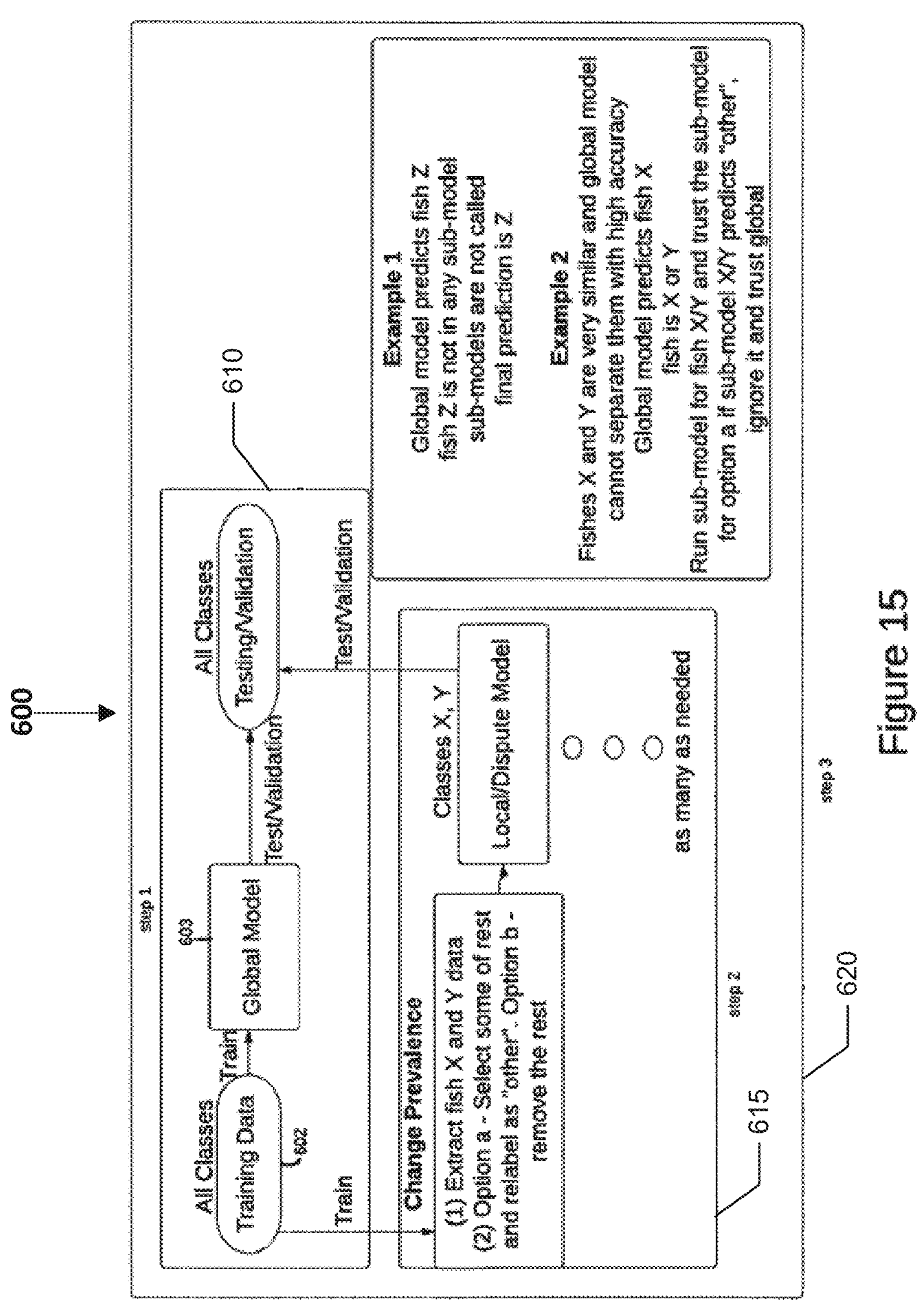
FIG. 15 depicts another method according to some embodiments presently disclosed.

Referring to FIG. 15, a method 600 is shown according to some embodiments presently disclosed. Although fish is being used, it is only an example and this method may be used on other products 230.

Presently disclosed sub-model technique allows to differentiate between fish species whose data are similar and the global model struggles to classify. The dataset is split into training and test sets. The sub-model technique may be implemented and evaluated as follows.

At 610, presently disclosed system and method may perform training and evaluation of the global model. The training set 602 is fed into a model 603 called Global Model to train it. The performance of the Global Model is evaluated using the test set. The confusion matrix is examined to identify low performance fish species. The fish species that the low performance species are predicted as are identified. Each set of similar fish species form a sub-model. Each sub-model either calls all the species not in that submodel "other" (option a) or removes them (option b).

At 615, presently disclosed system and method may perform training and evaluation of sub-model(s). The training data is relabeled to match each of the sub-model(s). Relabeled training data may be fed into each sub-model to train all the sub-models. The performance of each sub-model may be assessed against the test set.

At 620, presently disclosed system and method may implement and evaluate Global-plus-Sub-model. The test set may be fed into the Global model. If the predicted specie is not in any of the sub-models then the global model is passed as the prediction of the Global-plus-Sub-model. If the predicted specie is in any of the sub-models then the data point is fed into the sub-model and the prediction is passed as the prediction of the Global-plus-Sub-model. In option b, if the submodel predicts "other" then the Global model's prediction is passed as the global-plus-submodel's prediction. The performance of the Global-plus-Sub-model is compared with the performance of the Global model.

Figure 16:
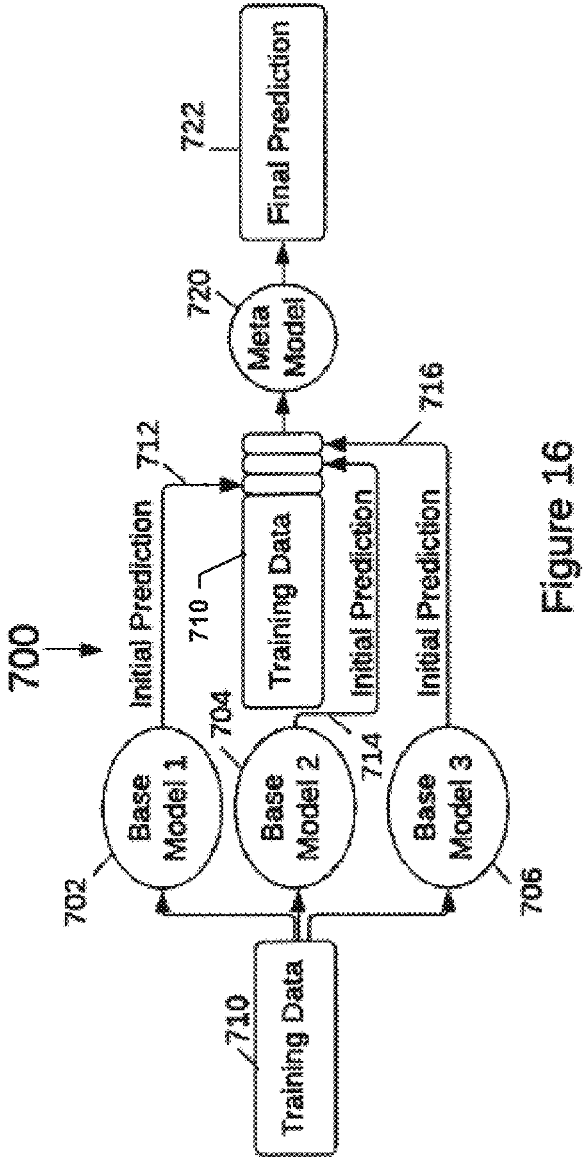
FIG. 16 depicts another method according to some embodiments presently disclosed.

Referring to FIG. 16, a method 700 is shown according to some embodiments presently disclosed. The method 700 is an ensemble stacking method for single mode spectroscopy. In stacking method, training data 710 is fed into three base models 702, 704, and 706. The base models 702, 704, and 706 may be selected to diversify the classification approaches. The base models 702, 704, and 706 may be, for example, k-nearest neighbor (KNN), random forest (RF) and logistic regression (LR). The initial predictions 712, 714, 716 of the base models 702, 704, and 706 are appended as features to the original training set 710. This new data set (i.e. combination of 710, 712, 714, 716) acts as the training set for another classification method 720. The classification method 720 may be, for example, Meta Model. Meta Model may be chosen based on performance, for example, linear discriminant analysis (LDA). Output of the classification method 720 is final prediction 722.

Figure 17:
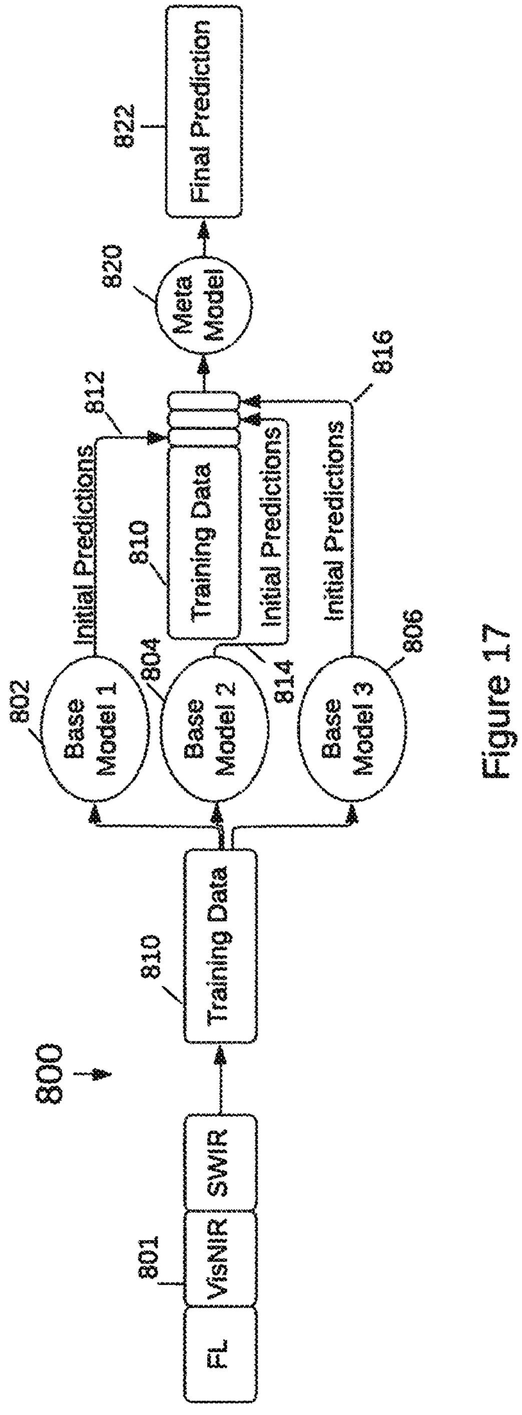
FIG. 17 depicts another method according to some embodiments presently disclosed.

Referring to FIG. 17, a method 800 is shown according to some embodiments presently disclosed. The method 800 is an ensemble stacking method with feature level fusion. According to some embodiments, data 801 is generated by concatenating data from the first fluorescence test, the second fluorescence test and the reflectance test to form one large data set 810. The data set 810 is fed into three base models 802, 804, and 806. The base models 802, 804, and 806 may be selected to diversify the classification approaches. The base models 802, 804, and 806 may be, for example, k-nearest neighbor (KNN), random forest (RF) and logistic regression (LR). The initial predictions 812, 814, 816 of the base models 802, 804, and 806 are appended as features to the original training set 810. This new data set (i.e. combination of 810, 812, 814, 816) acts as the training set for another classification method 820. The classification method 820 may be, for example, Meta Model. Meta Model may be chosen based on performance, for example, linear discriminant analysis (LDA). Output of the classification method 820 is final prediction 822.

Figure 18:
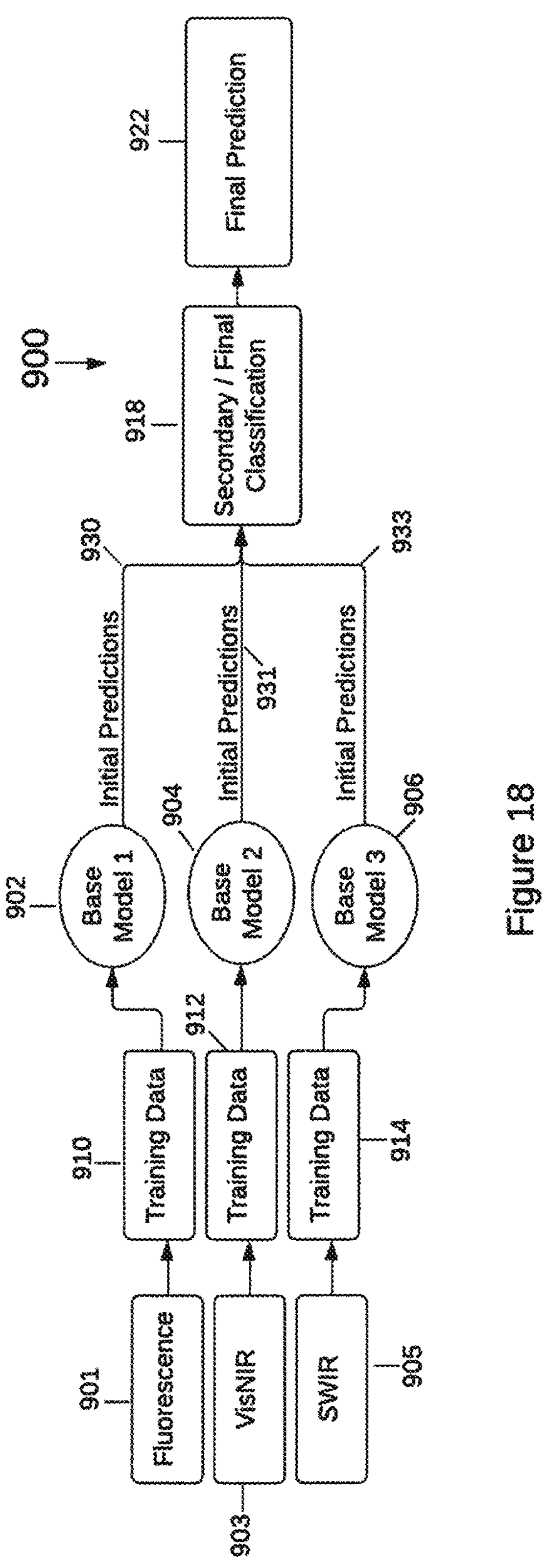
FIG. 18 depicts another method according to some embodiments presently disclosed.

Referring to FIG. 18, a method 900 is shown according to some embodiments presently disclosed. The method 900 is a decision level fusion with a decision-making mechanism 918 such as, for example, voting, weighted sum, etc. According to some embodiments, data 901, 903, 905 from each of the three spectroscopy modes (i.e. the first fluorescence test, the second fluorescence test and the reflectance test) are fed into its own base model 902, 904, 906. The base models 902, 904, 906 may be selected to diversify the classification approaches. The base models 902, 904, 906 may be, for example, k-nearest neighbor (KNN), random forest (RF) and logistic regression (LR). The initial predictions 930, 931, 933 from the Base Models 902, 904, 906 enter a decision-making mechanism 918. Output of the decision-making system 918 is final prediction 922. According to some embodiments, Base Models 902, 904, 906 may be used to predict the specie/freshness.

Figure 19:
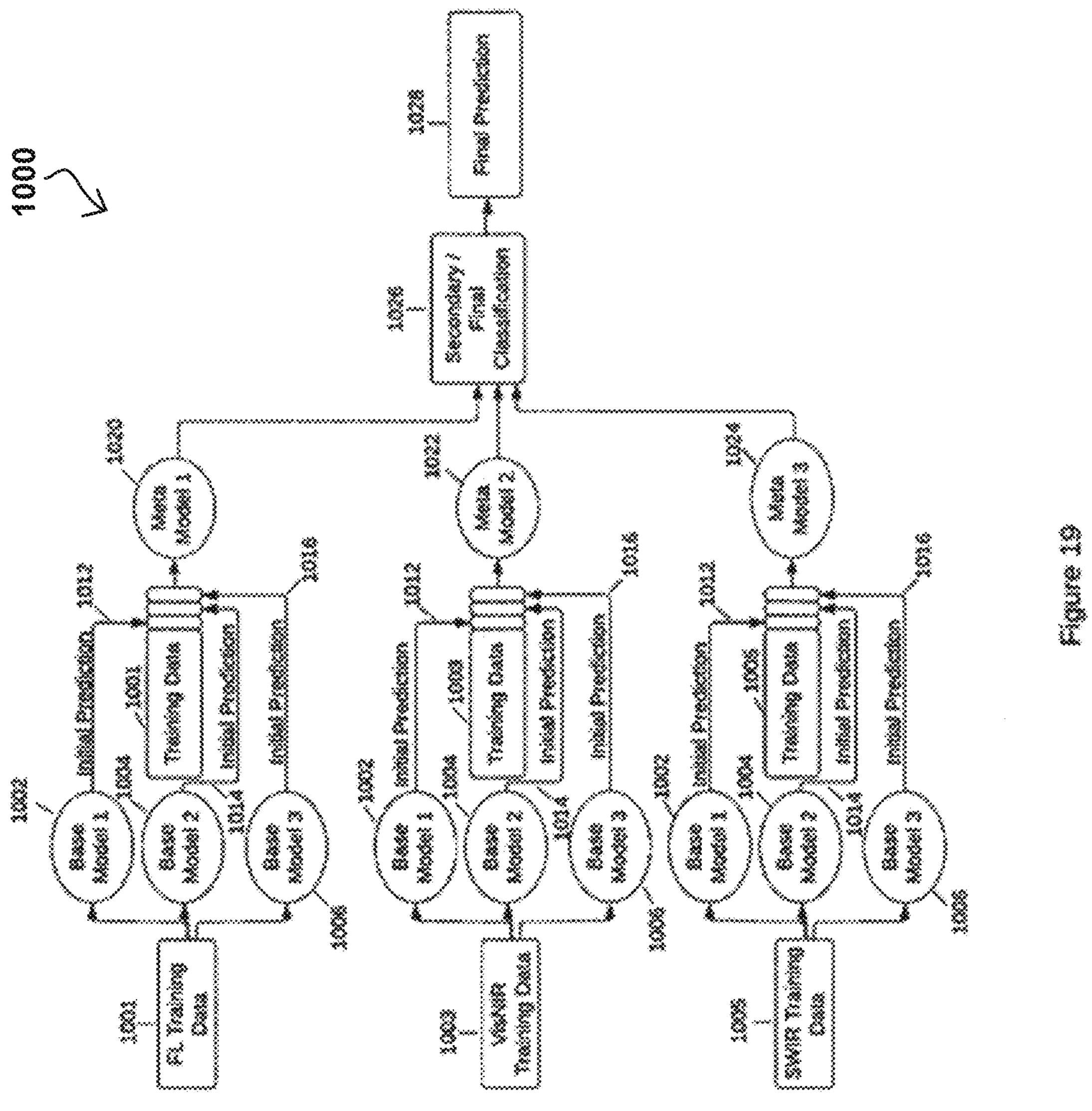
FIG. 19 depicts another method according to some embodiments presently disclosed.

Referring to FIG. 19, a method 1000 is shown according to some embodiments presently disclosed. The method 1000 is a decision level fusion with stacking and a decision-making mechanism 1026 such as, for example, voting, weighted sum, etc. According to some embodiments, data 1001, 1003, 1005 from each of the three spectroscopy modes (i.e. the first fluorescence test, the second fluorescence test and the reflectance test) are fed into multiple base models 1002, 1004, 1006. The base models 1002, 1004, 1006 may be selected to diversify the classification approaches. The base models 1002, 1004, 1006 may be, for example, k-nearest neighbor (KNN), random forest (RF) and logistic regression (LR).

The initial predictions 1012, 1014, 1016 of each of the base models 1002, 1004, and 1006 are appended as features to data 1001, 1003, 1005. The combination of 1001, 1012, 1014, 1016 acts as the training set for another classification method 1020. The combination of 1003, 1012, 1014, 1016 acts as the training set for another classification method 1022. The combination of 1005, 1012, 1014, 1016 acts as the training set for another classification method 1024. The classification methods 1020, 1022, 1024 may be, for example, Meta Model. Meta Model may be chosen based on performance, for example, linear discriminant analysis (LDA).

The output from the classification methods 1020, 1022, 1024 enter a decision-making mechanism 1026. Output of the vote system 1026 is final prediction 1028.

Using multiple base models may allow for diversity and for each model's predictions and errors to remain uncorrelated from each other. The meta model may also be trained on a dataset of just the base models' predictions and accuracies may be compared to evaluate the improvement due to ensemble stacking technique. LDA may be chosen for the meta model.

According to some embodiments, decision-making systems 918, 1026 may be implemented using, for example, majority vote, weighted sum, etc. When voting, the majority verdict may be deemed as the final prediction 922, 1028. In the low probability event where the predictions from the three spectroscopy modes happened to be different, the mode that consistently garnered the highest accuracy may be used.

According to some embodiments presently disclosed, the optical sensor 25 and the display 70 may be used to position the frontend assembly 182 directly over a predetermined area of the products to perform the three spectroscopy modes (i.e. a first fluorescence imaging mode, a second fluorescence imaging mode, and a reflectance imaging mode). According to some embodiments presently disclosed, a user of the device 10 may view the display 70 to view images generated by the optical sensor 25. Once the display 70 shows the area of the product to be tested, the user may perform the three spectroscopy modes on that area of product. According to some embodiments, the optical sensor 25 is aligned with the frontend assembly 182 so as to generate images on the display 70 of an area aligned with the frontend assembly 182.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another, i.e. may include transitory and/or non-transitory computer readable media. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

While several illustrative embodiments of the invention have been shown and described, numerous variations and alternative embodiments will occur to those skilled in the art. Such variations and alternative embodiments are contemplated, and can be made without departing from the scope of the invention as defined in the appended claims.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The foregoing detailed description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . . "

What is claimed is:

1. A system for assessing product, the system comprising:

an illumination hardware arrangement comprising transmission and sensing hardware, the illumination hardware arrangement configured to inspect a product using three modes from a group comprising:

a first fluorescence imaging mode;

a second fluorescence imaging mode; and a reflectance imaging mode; and processing hardware configured to operate the illumination hardware arrangement according to a protocol comprising inspection settings of the three modes, wherein the processing hardware receives scan results for the three modes from the illumination hardware arrangement and identifies attributes of the product by constructing a dataset from the scan results for three modes and analyzing the dataset; and an ensemble stacking technique including a performance chosen linear discriminant analysis meta model, wherein the meta model is trained on a dataset of multiple uncorrelated base models.

2. The system of claim 1, wherein the product comprises a pharmaceutical product, a drug product, biological product, meat, seafood, a construction product, a natural product, or a synthetic product.

3. The system of claim 1, wherein the processing hardware comprises a processor, at least one trained artificial intelligence module, and at least one classifier.

4. The system of claim 1, wherein the protocol is determined in part based on an identification of particular attributes expected to be associated with the product when examined using the three modes.

5. The system of claim 1, wherein the three modes are three spectroscopy modes.

6. A product inspection apparatus comprising:

an illumination hardware arrangement comprising transmission and sensing hardware, the illumination hardware arrangement configured to inspect a product using three modes from a group comprising:

a first fluorescence imaging mode;

a second fluorescence imaging mode; and a reflectance imaging mode; and processing hardware configured to operate the illumination hardware arrangement according to a protocol comprising inspection settings of the three modes, wherein the processing hardware receives scan results for the three modes from the illumination hardware arrangement and identifies attributes of the product by constructing a dataset from the scan results for three modes and analyzing the dataset; and an ensemble stacking technique including a performance chosen linear discriminant analysis meta model, wherein the meta model is trained on a dataset of multiple uncorrelated base models.

7. The product inspection apparatus of claim 6, wherein the product comprises a pharmaceutical product, a drug product, biological product, meat, seafood, a construction product, a natural product, or a synthetic product.

8. The product inspection apparatus of claim 6, wherein the processing hardware comprises a processor, at least one trained artificial intelligence module, and at least one classifier.

9. The product inspection apparatus of claim 6, wherein the protocol is determined in part based on an identification of particular attributes expected to be associated with the product when examined using the three modes.

10. The product inspection apparatus of claim 6, wherein the three modes are three spectroscopy modes.

11. The product inspection apparatus of claim 6, wherein the transmission hardware comprises one or more light sources.

12. The product inspection apparatus of claim 11, wherein the one or more light sources are light emitting diodes used in the first fluorescence imaging mode.

13. The product inspection apparatus of claim 11, wherein the one or more light sources are light emitting diodes used in the second fluorescence imaging mode.

14. The product inspection apparatus of claim 11, wherein the one or more light sources are bulbs used in the reflectance imaging mode.

15. The product inspection apparatus of claim 6, wherein the sensing hardware comprises at least two spectrometers.

* * * * *